(12) United States Patent
Yves

(10) Patent No.: US 9,029,801 B2
(45) Date of Patent: May 12, 2015

(54) APPARATUS AND METHOD FOR MEASURING A LUMINESCENT DECAY

(75) Inventor: Lacroix Yves, Tokushima (JP)

(73) Assignee: YSystems, Ltd., Tokushima (JP)

( * ) Notice: Subject to any disclaimer, the term of this patent is extended or adjusted under 35 U.S.C. 154(b) by 217 days.

(21) Appl. No.: 13/817,062

(22) PCT Filed: Feb. 15, 2011

(86) PCT No.: PCT/JP2011/053154
§ 371 (c)(1),
(2), (4) Date: Feb. 14, 2013

(87) PCT Pub. No.: WO2012/111093
PCT Pub. Date: Aug. 23, 2012

(65) Prior Publication Data
US 2013/0140431 A1    Jun. 6, 2013

(51) Int. Cl.
*G01N 21/66* (2006.01)
*G01N 21/64* (2006.01)
*H01L 21/66* (2006.01)

(52) U.S. Cl.
CPC ........ *G01N 21/6408* (2013.01); *G01N 21/6489* (2013.01); *G01N 21/66* (2013.01); *H01L 22/12* (2013.01); *H01L 2924/0002* (2013.01)

(58) Field of Classification Search
CPC .......... G01N 21/6408; G01N 21/6489; G01N 21/66; H01L 22/12; H01L 2924/00; H01L 2924/0002

USPC ................. 250/252.1, 458.1, 459.1
See application file for complete search history.

(56) References Cited

FOREIGN PATENT DOCUMENTS

| JP | 63-312649 | 12/1988 |
|----|-----------|---------|
| JP | 04-010574 | 1/1992 |
| JP | 07-014893 | 1/1995 |
| JP | 2006-519395 | 8/2006 |
| JP | 2008-170257 | 7/2008 |
| JP | 2010-517056 | 5/2010 |
| WO | WO 2004/079351 A1 | 1/2004 |
| WO | WO 2007/128060 A1 | 11/2007 |
| WO | WO 2008/094794 A1 | 8/2008 |

OTHER PUBLICATIONS

International Search Report and Written Opinion, International Application No. PCT/JP2011/053154, May 18, 2011, 8 pages.

*Primary Examiner* — Mark R Gaworecki
(74) *Attorney, Agent, or Firm* — Brinks Gilson & Lione

(57) ABSTRACT

A carrier lifetime measurement method includes material excitation, and detection of light emitted from that material. The method is characterized by: exciting the material such that excitation periods are repeated at periodic intervals; optically separating decaying light emitted after the end of the excitation period from light emitted from the material during the excitation period; and accumulating and detecting a plurality of the separated decaying light emissions within a measurement time which spans a plurality of the excitation periods and obtaining a lifetime based on an intensity of the accumulated light.

36 Claims, 22 Drawing Sheets

*non-ideal case of Illustration 10*

APPARATUS AND METHOD FOR MEASURING A LUMINESCENT DECAY

The present application is the national phase application of PCT Application No. PCT/JP2011/053154, filed Feb. 15, 2011, the entirety of which is hereby incorporated by reference.

TECHNICAL FIELD

This invention relates to a measurement method and to an apparatus for measuring the carrier lifetime of a material, by first exciting the carriers inside the material, then measuring the emitted light (luminescence).

BACKGROUND ART

The analysis of light emission or luminescence from a material is a wide-spread method for determining material properties such as impurity levels, crystal defects, in the field of semiconductors and other materials.

Some methods for generating luminescence include electroluminescence or photoluminescence. The free carriers (electrons and holes) are generated by applying electricity to the material, or generated by applying an excitation light source such as that of a laser, both resulting in light emission via the recombination of the electron-hole pairs.

The electron-hole pairs recombine spontaneously by some probabilistic time after their generation (either electrical or by light excitation). The typical time required for the process to decay is called decay time, or carrier lifetime. The carrier lifetime, as well as other characteristics of the emitted light (for example wavelength, intensity) can be used to determine the condition of the material by means of their dependence on impurities and defects inside the crystal.

In recent years, there has been a large increase in the demand for high efficiency solar-electric cells based on silicon, requiring better quality control and lower fabrication costs, as well as an increase in demand for larger area cells, hence the importance for high throughput fabrication methods of high quality large area silicon crystals.

The reduction of cracks and defects in the material used to make solar cells is crucial. Such cracks and defects absorb the electrical energy that the cell has converted from optical energy. In other words, the whole purpose of the solar cell, to generate electrical energy from light is wasted if the carriers of this energy encounter cracks which then converts this energy into heat. As explained until now, methods such as photoluminescence or electroluminescence are deeply related to the operation mechanism of solar cells. The characteristics obtained from these measurements, particularly the carrier lifetime, are also very sensitive to cracks, the types and level of impurity contents.

The conventional methods for analyzing solar cell efficiency are based on electrical biasing measurement methods, solar light simulation and others requiring physical contact with the device. Also these methods require the fabrication process to reach near completion before they can be performed. It is difficult to implement such processes in mass production environments without slowing down the fabrication or causing scratches and affecting the cleanliness due to contact application.

Another example of existing methods is described in Patent Literature 2, where time-correlated single photon counting methods or a streak camera method is used to obtain the carrier lifetime of a material. In the single photon counting method, the emission decay trace is measured directly however the time required to obtain the histogram is too long to be practically applied to the full wafer area. Whereas the streak camera method is forbiddingly costly.

PATENT LITERATURE

Patent Literature 1: European Patent Application Publication WO2007/128060A1
Patent Literature 2: Japanese Unexamined Patent Application Publication No. 2008-170257

DISCLOSURE OF THE INVENTION

Technical Problems Solved by the Invention

As mentioned so far, there is currently no method of measuring the carrier lifetime directly or obtaining information on cracks and impurity contents that is both fast enough to map a large area of the material, and at the same time not too costly to be used in material production environments.

The purpose of the present invention is to offer a new method and an apparatus using this method for obtaining information on the energy carriers, by monitoring the light emitted from a material without physical contact and at high speed, in order to implement a low cost carrier lifetime measurement system.

Furthermore, the present invention targets applications where the need for measuring the spatial variation of the carrier lifetime typically in semiconductors is imminent.

Means for Solving the Problems

The carrier lifetime measurement method in the present invention consists of obtaining an integrated intensity via accumulated light emitted from a material. This emission is induced by periodically repeated carrier excitations. Decaying emissions follow immediately, are optically separated from the emission occurring during the excitation, and integrated during a time which spans several periods of the excitation cycles.

In order to separate the aforementioned decaying emissions that follow the excitation, from the emission occurring during the carrier excitations, the light accumulation may start precisely at the end or after the end of each excitation period, or even partway through the excitation period.

Included in the present invention, is a means for periodically modulating or intermittently blocking the excitation source before it is applied to the material.

Included in the present invention, is also a means for periodically modulating or intermittently blocking the light emitted from the material before it reaches the light accumulation device.

In the present invention, the light accumulation device can be an array of several detector cells, each of which accumulating light spanning several periods of the decaying emission cycles. For example, the detector cells may be arranged in a two dimensional array in order to measure simultaneously the carrier lifetime of an area of the material. Also another method included in this invention can be described a line of detectors moving across the material in order to also obtain the information related to the carrier lifetime of an area on the material.

The present invention includes a method where multiple measurements of the lifetime are measured as described above, with increasing modulation frequencies until a non-linear change in the integrated intensity is detected. Using this frequency dependence, it is possible to quantify the lifetime information. Furthermore, taking the ratio of the intensities at different frequencies, it is possible to normalize the intensity dependence of the emission and isolate the carrier lifetime dependence, making it possible to compare areas of different emission intensities.

The present invention includes the method of comparing intensities measured at a given modulation frequency to that of the intensity measured without modulation also in order to remove the intensity component of the emission and make possible the isolation of the carrier lifetime component.

The above method for isolating the carrier lifetime component of the intensity is also possible by taking the ratio of intensities measured at different modulation waveforms Again, the method for isolating the carrier lifetime component of the intensity is also possible by taking the ratio of intensities measured at modulations which are relatively offset in phase.

Moreover, the carrier lifetime component isolation of the intensity is possible by comparing intensities for measurements using intermittent excitation of different duty ratios, where opposite duties are applied to the excitation side compared to the detection side.

The present invention includes the methods where the excitation applied to the material is either optical or electrical.

The carrier lifetime measurement apparatus of the present invention consists of an excitation apparatus for exciting energy carriers in the material and a detecting apparatus which accumulates the resulting light emission from that material. The present invention also implies an inspection system which may contain such an apparatus. It uses the accumulated optical signal, for which the excitations are periodically applied and immediately followed by decaying emission. These emissions are optically filtered before reaching the light accumulation device while the intensity integration spans several periods of the decaying emission cycle.

The apparatus of the present invention includes an excitation source and a modulation apparatus to generate the above mentioned periodicity in the excitation.

This excitation source can be of either optical or electrical nature.

The apparatus of the present invention includes an apparatus for separating the light emitted by the material when it is emitted during the excitation, from the light emitted by the material during the decaying emission period. This apparatus can be a light modulating apparatus, or an apparatus that periodically blocks the light, while a plurality of decaying emission light cycles can be spanned during the integration by the light accumulation device.

In the apparatus mentioned above which includes an apparatus for separating the light emission from the material between the light emitted during the excitation and the light decaying after excitation, the present invention includes the cases when the light accumulation starts precisely at the end, or after the end of the repeated excitation period, or even partway through the excitation period.

The apparatus of the present invention can be made using a multitude of detector cells arranged in an array, each of which accumulates light spanning several periods of the decaying emission cycles. In this case, the detector cells may be arranged in a two dimensional array in order to measure simultaneously the carrier lifetime of an area of the material, obtaining a correspondence between a position on the material and a detector cell along with the respective information related to the carrier lifetime. Another configuration for the above included can be a line of detector cells positioned normal moving across the material in order to also obtain the information related to the carrier lifetime of an area on the material.

The apparatus of the present invention may also have a wavelength filter or light polarizing filter between the material and the light detection device.

The apparatus of the present invention for which includes a periodic excitation apparatus, can be constructed such that a control section makes use of the integrated intensity measured as described above for different excitation cycle frequencies, to compare them in order to remove the intensity component of the signal, and to isolate and quantify the carrier lifetime component.

Also the apparatus of the present invention for which includes a periodic excitation apparatus, can be constructed such that a control section makes use of the integrated intensity measured as described above for different excitation cycle frequencies, then compare them with the intensity measured continuously in order to remove the intensity component of the signal, and to isolate and quantify the carrier lifetime component.

Also the apparatus of the present invention for which includes a periodic excitation apparatus, can be constructed such that a control section makes use of the integrated intensity measured as described above applying different periodic modulation waveforms, to compare them in order to remove the intensity component of the signal, and to isolate and quantify the carrier lifetime component.

Also the apparatus of the present invention for which includes a periodic excitation apparatus, can be constructed such that a control section makes use of the integrated intensity measured as described above applying different relative phase shifts of the modulation, then compare them with the intensity measured continuously in order to remove the intensity component of the signal, and to isolate and quantify the carrier lifetime component.

Also the apparatus of the present invention for which includes a periodic excitation apparatus, can be constructed such that a control section makes use of the integrated intensity measured as described above applying different excitation duty ratios of opposite phase between the excitation and the detection, then compare them with the intensity measured continuously in order to remove the intensity component of the signal, and to isolate and quantify the carrier lifetime component.

Effect of the Invention

The present invention enables the measurement of information related to the carrier lifetime inside of a material, without physical contact, by monitoring the light emitted from that material.

Moreover, this invention makes it possible to measure the uniformity of the carrier lifetime over an area of the material.

DETAILED DESCRIPTION OF THE PREFERRED EMBODIMENTS

Figure 1:
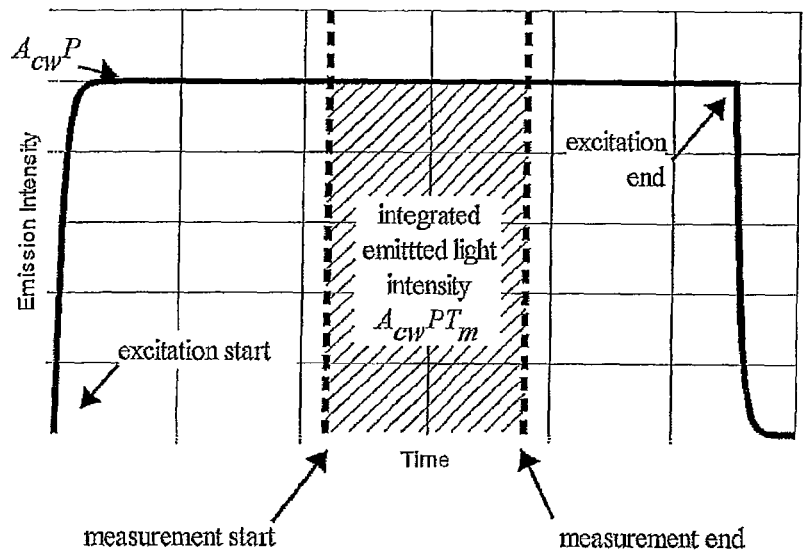
FIG. 1 Graph describing the intensity of the light emitted from the material during excitation, FIG. 2 Graph showing the decay curves of the emission due to the carrier lifetime in the material, FIG. 3 Diagram showing a change in the intensity of the light emitted from the material when given a square wave excitation, FIG. 4 Block diagram of the measuring apparatus and measuring method for detecting light emission from the material modulated with opposite phase with respect to the excitation modulation.

In order to evaluate a material such as a semiconductor, the current invention measures the light emitted (luminescence) from that material.

The energy of a non-valence electron in the crystal of a material is determined by the position of the conduction band, but can also be determined by a variety of states such as non-radiative centers, impurity levels, or other defect states. If an electron is in a non-thermal-equilibrium excited state, it will eventually recombine with a hole within a probable time giving rise to a carrier lifetime. That recombination causes an energy conversion which can be in the form of light emission, or in the form of vibrations or heat in the material. If the carrier recombines due to defects, impurities or cracks in the crystal, then the probability of emitting light due to natural recombination will be reduced. Because of this, in general the carrier lifetime is shorter in the presence of a high density of crystal defects. Therefore a measurement of the carrier lifetime is an important means of evaluating the material's defect levels and its crystal quality.

It is important for crystalline solar cells to have low defect densities. If electrons (energy carriers) excited by the absorption of solar light get trapped by defect states, their energy gets reconverted to light or transformed into heat such that this electrical energy can no longer be extracted. Again In solar cells the carriers generated by light absorption are converted to electricity once they reach the electrodes, however if these electrodes are not within the distance that the carriers can travel in their lifetime, the electricity cannot be generated. Therefore longer carrier lifetimes allow for larger the distance between electrodes and hence leaving more area for light absorption.

The ability to measure the carrier lifetime distribution across the entire solar cell surface without contact and at high speed would enable the monitoring of the solar cell manufacturing process, especially between individual processing steps. For example, even before the solar cell fabrication process is completed, within the steps required to form the necessary high quality p-n junction, crystal growth, ion implantation, conducting layer annealing or other non-reversible processes, measurement of the carrier lifetime across the entire surface would allow an evaluation immediately after that very step. Based on the result expressed as an image of the carrier lifetime uniformity, not only could the process be halted and defective material not be allowed to continue into production, but also this information could be used to pinpoint the problematic areas and help improve the production yield.

The present invention seeks to provide a low cost and high speed method and apparatus for measuring the carrier lifetime of a material via contact-less monitoring of the material luminescence. It is characterized by its ability to distinguish or separate the light emitted during carrier excitation from the light emitted after this excitation. It is further characterized by the ability to record a signal based on the repeated accumulation of the separated light.

In the embodiments below, photoluminescence is used to evaluate the carrier lifetime. In photoluminescence, light is used to excite the electrons which recombine with holes to emit light. However the present invention is not limited to photoluminescence and the present invention can also be carried out using electroluminescence where the excitation process is electrical.

FIG. 1 shows a graph representing the continuous excitation and luminescent emission for a wafer such a silicon at a given position, where the horizontal axis is time and the vertical axis is emission intensity. Ideally the continuous intensity of the luminescence has an amplitude given by AcwP, where Acw is the amplitude of the excitation, and P is the probability that the excited energy gets reconverted to light. The hatched area represents the integrated intensity AcwPTm of the luminescence during a time Tm during which the measurement takes place. Although the carrier lifetime plays a role in the process described here, that specific information cannot be extracted from the integrated intensity value.

Figure 2:
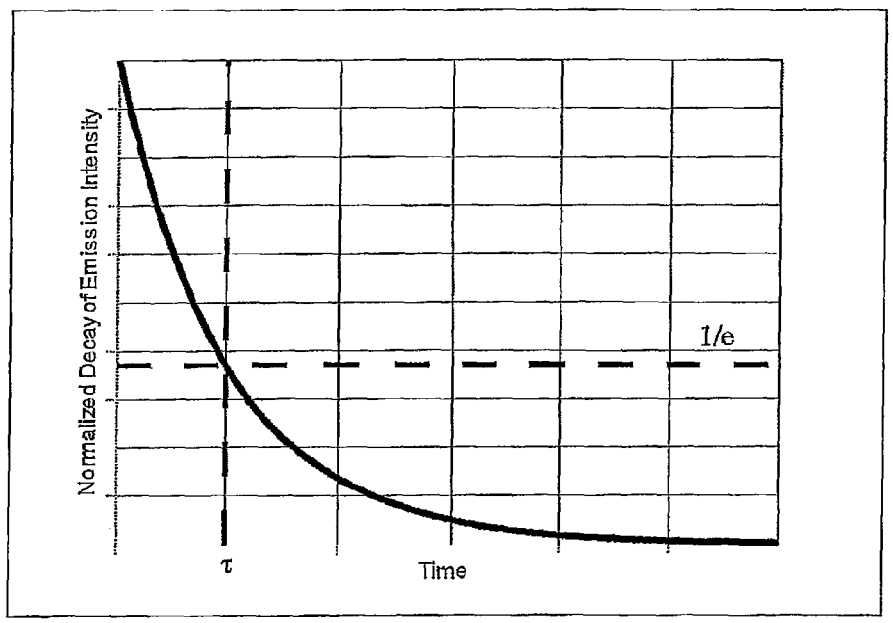

FIG. 2 shows a graph representing the decaying light emission from a material such as silicon after light excitation, and the corresponding carrier lifetime position, with time as the horizontal axis and normalized emission intensity as the vertical axis.

With some probability P, once a photon is absorbed it can be re-emitted as a photon of lower energy, after a time $\tau$ determined by the material characteristics. When an infinite number of photons follow this process, the probabilistic distribution is described by an exponential decay curve. Ideally, for an excitation described by the delta function $A\delta$, the probability distribution for the light re-emission is $APe^{-t/\tau}$ (where e is the natural number) as shown in FIG. 2. This time $\tau$ is to be defined as the carrier lifetime. In other words, the carrier lifetime $\tau$ can be described as the time required for the 1/e fraction of the luminescence to decay with respect to its initial intensity.

However, when attempting to measure this time $\tau$, extremely high speeds and at the same time extremely high sensitivity and timing precision is required of the instrument in order to accumulate the average characteristic of many photons. Also in order to average enough photons for carrier lifetimes in the microsecond range, a relatively long measurement time is required. Moreover since the measurement of very weak light emission is necessary, the background signal level due to usual instrument noise makes the task substantially difficult.

Figure 3:
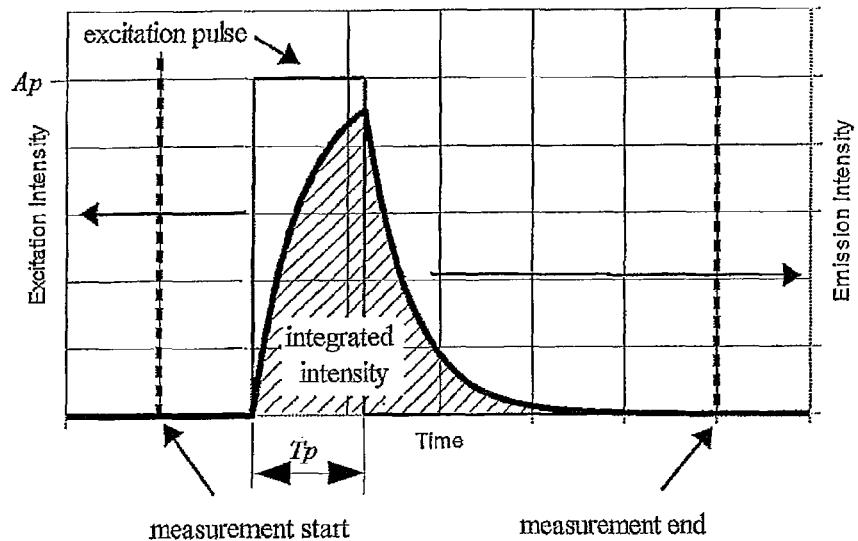

The graph of FIG. 3 shows the relationship between time and the emission intensity from the material when given a sharp pulse of excitation.

The thick continuous line of FIG. 3 describes the light emission. The curve shows an increase of intensity during the sharp pulse, followed by a decrease in emission after the end of the excitation. The time integrated intensity of this emission, described as the hatched region in FIG. 3, resulting from an excitation pulse of amplitude Ap during a time Tp, is simply PTpAp. This accumulated intensity of the emission has dependence on the emission probability P, however the carrier lifetime component still cannot be separated or extracted from it.

However, the emission shown in FIG. 3 shows the characteristic described in FIG. 2 of the exponential decay $APe^{-t/\tau}$ on the falling edge in which carrier lifetime parameter $\tau$ is convoluted.

In the present invention, the decaying emission portion of FIG. 3, following the increase and decrease of the excitation, is isolated in order to measure the carrier lifetime. However in order to extract and measure only that portion of the emission, since the pulse duration can be very short, a very fast device for detecting the light is necessary. Also since the decaying emission intensity can be very weak, it is necessary to have an apparatus that continuously and repeatedly acquires the emission signal in order to obtain a reasonable signal.

Figure 4:
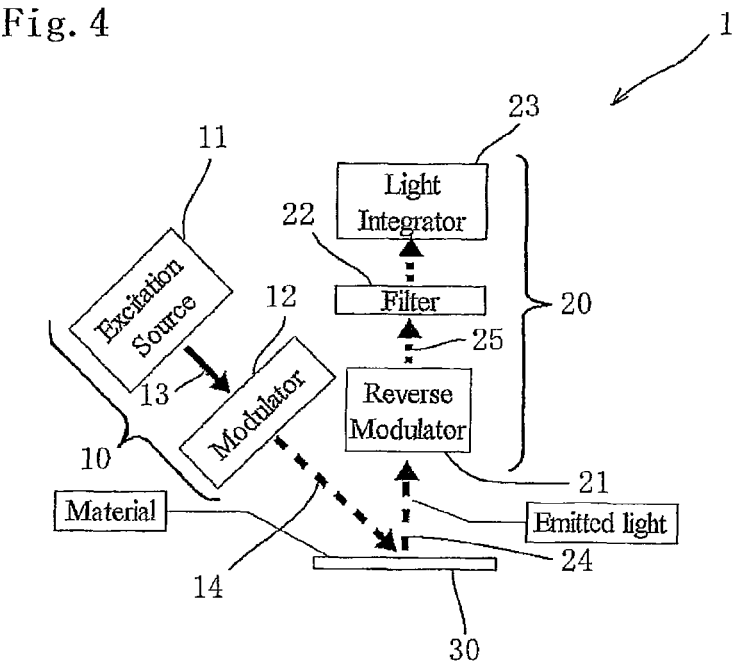

The basic embodiment of the present invention's apparatus and measurement method is described in the block diagram of FIG. 4, where an excitation is applied to a material, and the resulting multiply repeated and extracted decaying light emissions from that material are measured.

The apparatus 1 of FIG. 4 contains an excitation apparatus 10 and a detecting apparatus 20. The excitation apparatus 10 includes an excitation source 11 and a modulation device 12. The detecting apparatus 20 is composed of a modulation device 21, a filter 22 and a light accumulation device 23. The excitation source 11 is typically a continuous emission solid state laser while 12 and 21 are acousto-optic modulators. 23 is a device that integrates light by accumulating it over time and at specific positions, such as for example a CCD (charge coupled device) array. 22 is a wavelength filter or an optical polarization filter.

Figure 5:
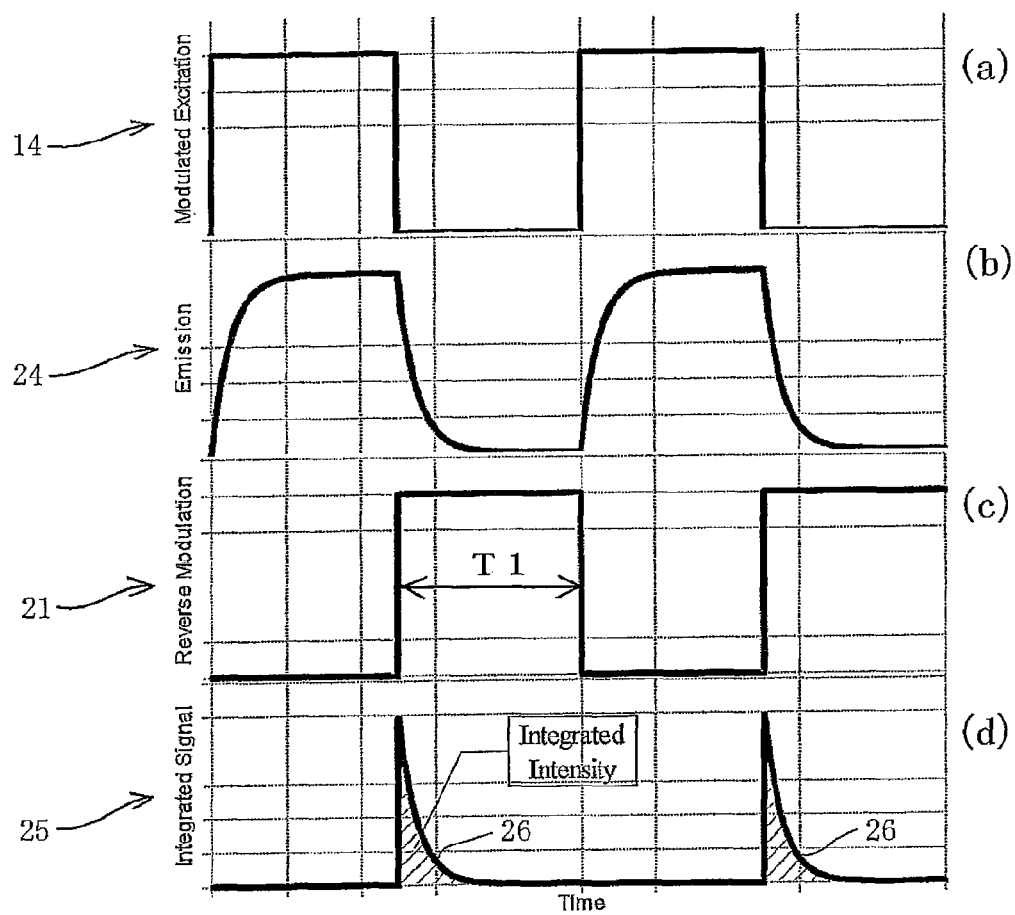
FIG. 5 Diagram showing the modulated excitation when using a measuring apparatus shown in FIG. 4, the waveform emitted from the material, the detector side modulation and the resulting separation of the decaying emission.

The light 14 has a waveform described by excitation emitted by 11 and modulated by 12 and is shown in FIG. 5 (a). The continuous light 13 of FIG. 4 enters the acousto-optic modulator 12 which rapidly switches its refractive index to allow light to pass. The intensity of the resulting light intensity at 14 therefore rises and drops in a square wave manner as described in FIG. 5 (a). The modulated light 14 shown in FIG. 5 (a) has a duty ration of 50%.

The luminescence 24 emitted from a semiconducting material 30 such as silicon excited by the modulated excitation 14 has intensity variations shown in FIG. 5 (b). Just like described in FIG. 3, the luminescence 24 sharply rises in intensity upon the start of the sharp excitation rise of 14, then shows decaying intensity when the excitation drops.

The modulation waveform applied by the modulation device 21 on the detection side of the apparatus is shown in FIG. 5 (c). The modulator 21 is designed to be reversely synchronized with the modulated excitation 14 waveform shown in FIG. 5 (a), in such a way that when the excitation intensity drops in 14, the light begins to be allowed through in the acousto-optic modulation 21. Both modulators 12 and 21 and thus synchronized using a control signal and set to operate in such a mutually reversed modulation.

The separated light 25, originating from the light 24 emitted from the semiconductor material 30 due to the modulated excitation 14, and allowed to pass by the modulator 21 is shown in FIG. 5 (d). The light allowed to pass through begins at the end of the excitation 14 therefore only contains the decaying intensity portion of the emission as shown in the hatched area 26.

As described in FIG. 5 (d), applying a mutually reversed synchronized modulation such as in FIG. 5 (c) is ideal for extracting only the decaying portion of the emission 26 from the luminescence 24.

In addition, FIG. 5 (b) represents the emission 24 of a single point from a certain area on the semiconductor material 30 from which the decaying light 26 is separated. The area of that single point is then reflected as a single pixel or cell of the CCD detector array in the detection apparatus 23.

The intensity of light 25 shown in FIG. 5 (d) then passes through filter 22 before reaching the detecting device 23, so that only some components of the decaying light 26 are extracted. The CCD detector cells of the detecting device 23 accumulate light during a certain integration time and the integrated intensity is then stored in memory. With respect to this integration time, the modulations of FIGS. 5 (a), (c) are much faster such that several cycles of the decaying light 25 shown in FIG. 5 (d) can be accumulated in a single measurement.

As described in FIGS. 2 and 3, the carrier lifetime τ characterizes the light 26, the decaying part of the emission immediately following the end of the excitation, and this light is accumulated multiple times by the measurement apparatus in order to effectively extract the carrier lifetime information.

Although the light 26 generated by the excitation light 14 is weak, The process of rapidly applying the modulations shown in FIGS. 5 (a) and (c) makes it such that several occurrences of the decaying light 26 are accumulated during the integration time. In result, the signal due to the light accumulated by the detecting device 23 from the light 26 can be high enough compared to the detector's and other sources of noise, and a significant signal can be extracted.

Figure 6:
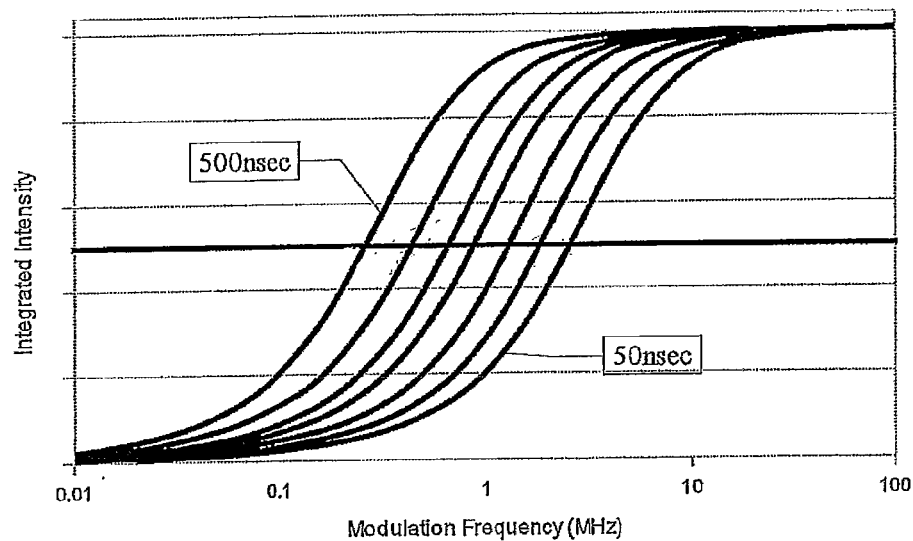
FIG. 6 Graph showing the relationship between the intensity of the accumulated light detector output with change in the modulation frequency of the excitation given to the material of different carrier lifetimes.

The decay light 26 accumulated by the detecting device 23 as an integrated intensity, and normalized with respect to their high frequency saturation value, is shown in the graph of FIG. 6, plotted as a function of the frequency of the excitation and detection modulation devices 12 and 21. The vertical axis shows the intensity, and the horizontal axis the modulation frequency. The resulting simulation of the intensity, for a fixed integration time, is shown in FIG. 6 where the curves for discrete steps of material carrier lifetime of 50 nsec, 70 nsec, 100 nsec, 150 nsec, 200 nsec, 300 nsec and 500 nsec are plotted.

The graph of FIG. 6 shows that at low modulation frequency, when the modulation period is much longer than the carrier lifetime parameter τ, nearly no light or relatively very little of the emission decay light 26 is accumulated during the integration time. And as the frequency is increased, proportionally more and more of decayed light 26 is accumulated so that the intensity increases linearly.

Furthermore, as the frequency increases and the period of the modulation T1 shown in FIG. 5 (c) of the luminescence 24 approaches the carrier lifetime parameter τ, a super-linear increase in the intensity is observed. A further increase of the modulation frequency eventually causes the accumulation of the decaying light 26 to saturate, and as such the intensity measured eventually saturates as shown in FIG. 6.

When the excitation modulation device 12 operates at a duty ratio of 50% and the detection modulation device 21 operates at a duty ratio of 50%, the theoretical saturation level of the intensity is ¼ of the luminescence intensity AcwP shown in FIG. 1 for the case of continuous excitation.

FIG. 6 shows a solid line at 50% of the saturation intensity for a series of different carrier life times. Near the crossing of the integrated intensity of each curve and the 50% line, a region of near-linear trend is seen as function of the logarithmic frequency scale is seen.

A frequency in this range is desirable when selecting a single frequency for the excitation modulation frequency and the detection modulation frequency of the modulations shown in FIGS. 5 (a) and (c) respectively. In this case FIG. 6 shows that the normalized integrated intensity will increase for a longer carrier lifetime, or decrease for a shorter carrier lifetime.

Again, assuming the same emission efficiency giving rise to the same emission intensity AcwP for several points on a material, and using the same excitation modulation frequency (detection modulation frequency), then each of the measurement intensity should represent the carrier lifetime for that corresponding region of the material. For long carrier lifetime the measured intensity should be high, and for short carrier lifetime the measured intensity should be low, such that the value of the carrier lifetime is directly represented by the intensity of the measured signal.

Figure 7:
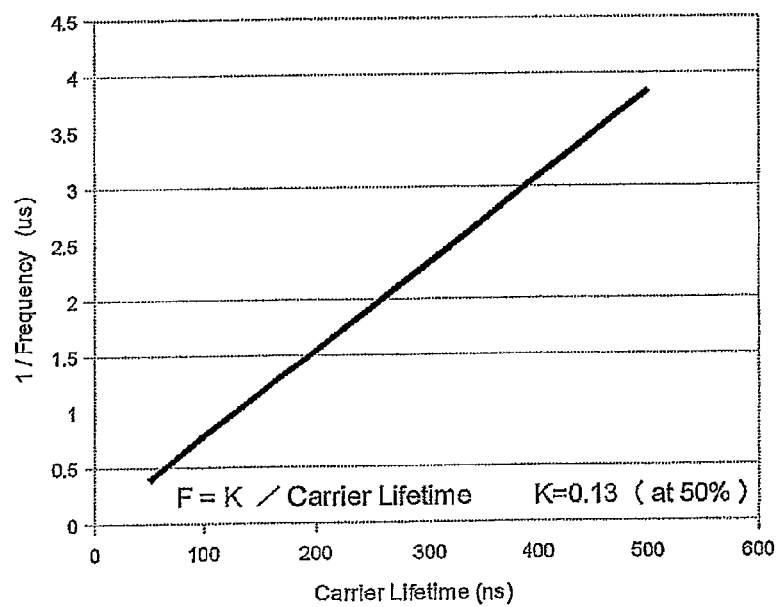
FIG. 7 Graph showing the relationship between frequencies at which the integrated decay light intensity is 50% of its maximum value, as a function of the carrier lifetime.

Then based on the simulation of FIG. 6, the relationship between the crossing frequency of each plotted line for each nominal carrier lifetime, where the intensity reaches 50% of its saturated value, and the carrier lifetimes, is plotted in the graph of FIG. 7. The horizontal axis shows carrier lifetime, and the vertical axis 1/frequency or in other words the modulation periods described in FIGS. 5 (a) and (c) and for which the intensity reached 50% for the nominal carrier lifetime in that material.

The result obtained from the simulation shown in FIG. 7 is a linear relationship between the carrier lifetime and the modulation at which the measured intensity is 50% of its saturation value and this relationship can be expressed by a parameter K=0.13. In other words if the modulation frequency at which the integrated intensity is 50% of its saturation value is known as F, then the carrier lifetime TX is given by τx=0.13/F. In addition, the relationship described in FIG. 7 is not limited to the carrier lifetime range 50 nsec to 500 nsec.

Also the above relationship is not limited to the crossing when the integrated intensity reaches 50% of its saturation value. A similar linear relationship can be obtained for relative intensity crossings of, for example, 40% or 60%.

The variations in the above light intensity are dictated by both the material's ability to emit light, or the probability of light emission giving rise to the intensity AcwP, and the carrier lifetime component of the emission. However as explained using FIGS. 5 and 6, by sweeping the modulation frequency it is possible to precisely quantify the carrier lifetime component.

Moreover, once the carrier lifetime has been quantified for 1 point on a material, it is possible to extract and quantify other points by simply using measurements at 2 fixed modulation frequencies, and taking the ratio between the two intensities in order to remove the intensity (light emission probability) component. Using this method it is not necessary to sweep the modulation frequency in order to isolate and quantify the carrier lifetime, hence a high speed measurement of the carrier lifetime becomes possible. This measurement method is explained in the following.

Figure 9:
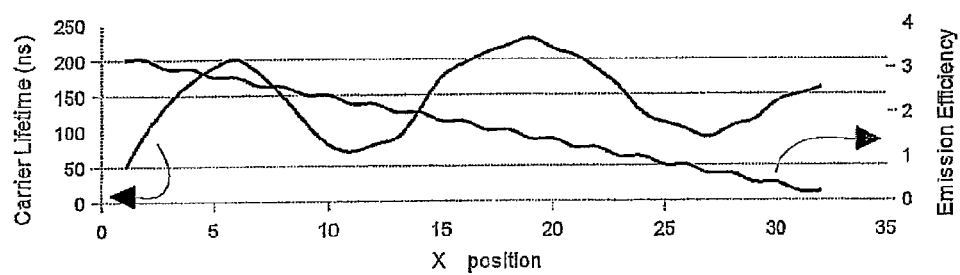
FIG. 9 Graph showing material data used for simulation in the following graphs. The data represents a change in carrier lifetime values and emission efficiency values as a function of position (x axis) on the material.
Figure 10:
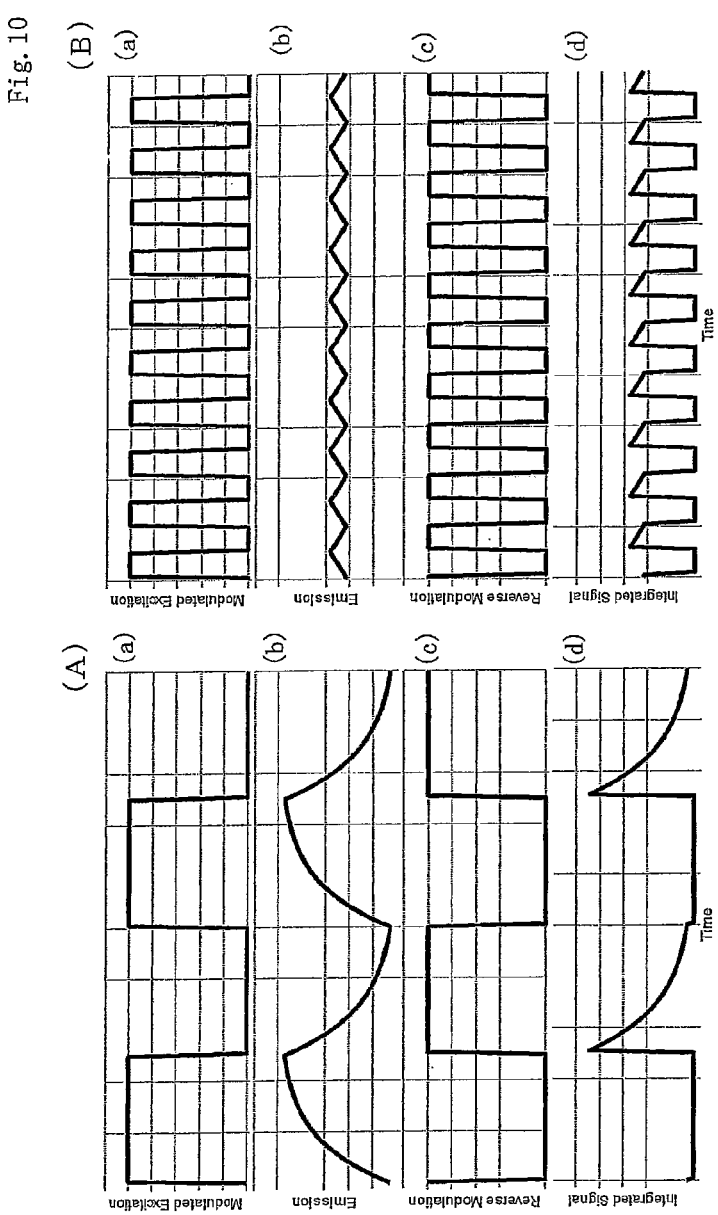
FIG. 10 Diagram showing the modulated excitation, the waveform emitted from the material, the detector side modulation and the resulting separation of the decaying emission, for a change in modulation frequency.
Figure 11:
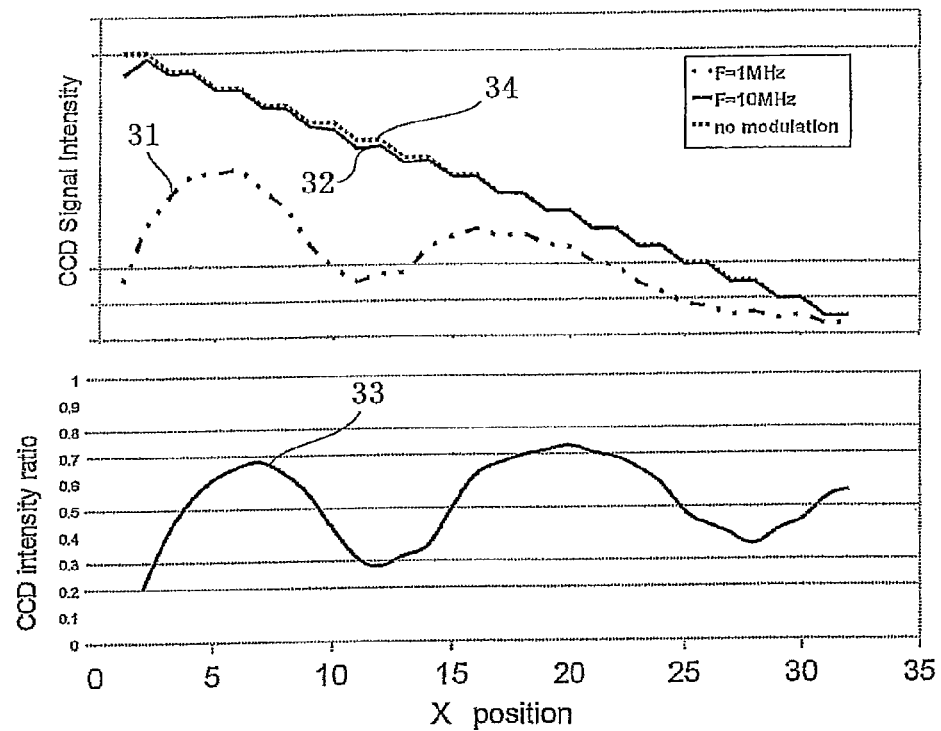
FIG. 11 Graph showing the integrated intensity as a function of position on the material simulated using the data of FIG. 9, when the two frequencies shown in FIG. 10 and in the case of no modulation, and the ratio of the intensity taken at the two frequencies.

FIGS. 9 through 11 show the simulated results of a method for extracting the carrier lifetime information, using assumed material properties of the emission probability and carrier lifetime as a function of position.

FIG. 9 shows the hypothetical simulation data for a material that has relatively different properties and trends for the emission probability and the carrier lifetime as function of position. The horizontal X axis represents position on the material. This material is assumed to have emission efficiency slowly decreasing from the left toward the right, while its carrier lifetime characteristics vary in a sort of wave-like trend as shown in the Figure.

Given a single position on the X axis of FIG. 9, the simulated measurement at 1 MHz modulation is shown in FIG. 10 (A), where the applied excitation modulation 12 and the detection modulation 21 are reversed in phase. The waveforms of FIG. 10 (A) are the same as those shown in FIG. 5, (a) the excitation modulation waveform, (b) the waveform of the luminescence emitted from the material, (c) the detection side modulation, and (d) the resultant separated decaying portion of the light intensity.

By accumulating the separated light described in FIG. 10 (A) (d) during a given integration time using a CCD detector, an integrated intensity is obtained. FIG. 11 shows a graph of this intensity as a function of position for a modulation frequency of 1 MHz as curve 31 plotted in a double dotted dashed line.

Just as in FIG. 10 (A), FIG. 10 (B) shows (a) the excitation modulation waveform, (b) the waveform of the luminescence emitted from the material, (c) the detection side modulation, and (d) the resultant separated decaying portion of the light intensity, where the applied excitation modulation 12 and the detection modulation 21 are reversed in phase, however for a modulation frequency of 10 MHz. In FIG. 11, the resulting integrated intensity as a function of position is shown as curve 32 plotted in a continuous line.

By taking the ratio of the intensity distribution obtained at 1 MHz curve 31 with respect to the intensity distribution curve 32 obtained at 10 MHz, one obtains curve 33 also shown in FIG. 11. This curve closely resembles the original carrier lifetime data of FIG. 9, demonstrating how taking the ratio of measurements obtained at 2 different frequencies allows the extraction of the carrier lifetime information.

Figure 8:
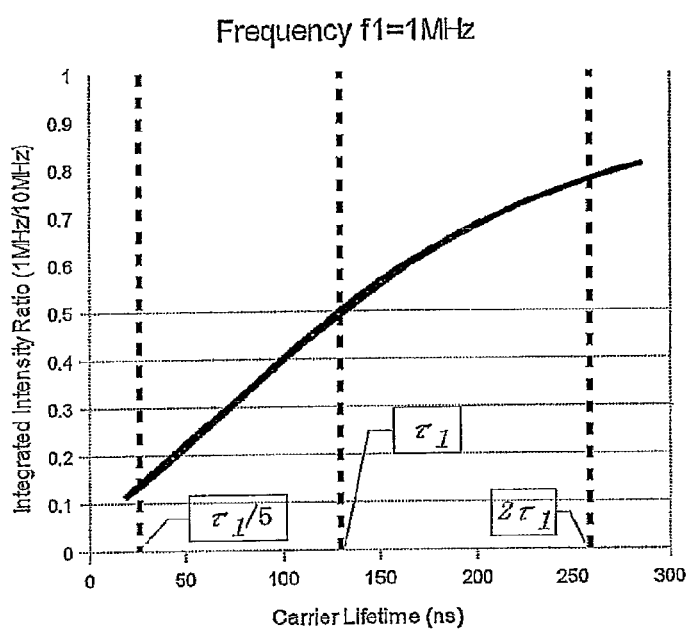
FIG. 8 Graph showing the relationship between the integrated intensity at a given frequency, which has been normalized with the intensity obtained at ten times that frequency, and carrier lifetime, in the case of square modulation.

The result of the simulation of FIGS. 9 to 11 is also shown in FIG. 8 where the ratio of the intensities obtained by integrating the light 26 at 1 MHz versus the intensities obtained by integrating the light 26 at 10 MHz for the distribution of material properties is plotted in the vertical axis as a function of the carrier lifetime parameter τ in the horizontal axis. Also shown are nominal carrier lifetimes τ1=130 nsec, τ1/5 and 2τ within which the material properties of FIG. 9 fluctuate.

As shown in FIG. 8, the relationship between the obtained measurement intensity and the carrier lifetime is nearly linear. From this it can be concluded that taking the ratio of 2 integrated intensities measured at different modulation frequencies, it is possible to normalize the intensity for different material emission probability AcwP, in order to obtain a signal which represents the change in the carrier lifetime.

Figure 12:
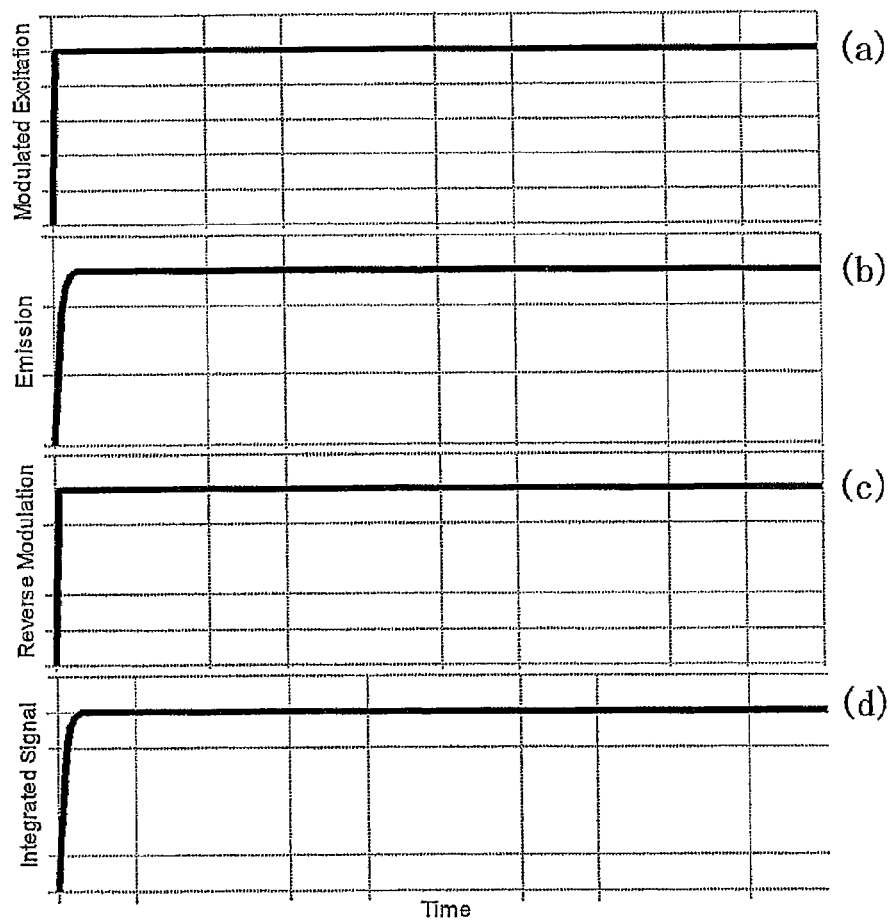
FIG. 12 Diagram showing the non-modulated excitation, the emitted signal from the material, the detector side non-modulated trace and the resulting integrated signal.

The case where no modulation is applied to the excitation or to the emitted light is shown in FIG. 12. The continuous excitation is shown in (a), the resulting luminescence in (b), the lack of detection modulation in (c) and the resulting unaffected continuously excited luminescence reaching the CCD detector is shown in (d).

The corresponding integrated intensity from the accumulation of the light reaching the CCD detector described in FIG. 12 is also shown in FIG. 11, after dividing this intensity by 4. The curve 34 is therefore ¼ of the emitted at continuous excitation plotted as function of position. A close resemblance is seen when comparing curve 32 obtained at 10 MHz to curve 34. Therefore it is reasonable to state that taking the ratio of curve 31 measured at 1 MHz with ¼ of the intensity obtained during continuous excitation without any applied modulation will result in approximately the same curve 33.

Hence normalizing integrated intensity of the modulated luminescence with the continuously excited luminescence enables the extraction of the carrier lifetime information.

In the above explanation, using the preferred embodiment describe, the excitation modulation of 12 and the detection modulation of 21 were assumed to have perfectly sharp square wave rise and drop characteristics, and moreover to be operating in perfect synchronization. However an actual modulating device may not have the inability to produce such a square wave, slight deviations from perfect synchronizations and also the effects of noise in the system may affect the final modulation waveform characteristics.

However the present invention's method and apparatus can still extract the information related to the carrier lifetime as described above, even though deviations from perfect timing, from ideal excitation modulation waveform or from ideal detection modulation waveforms exist.

Figure 13:
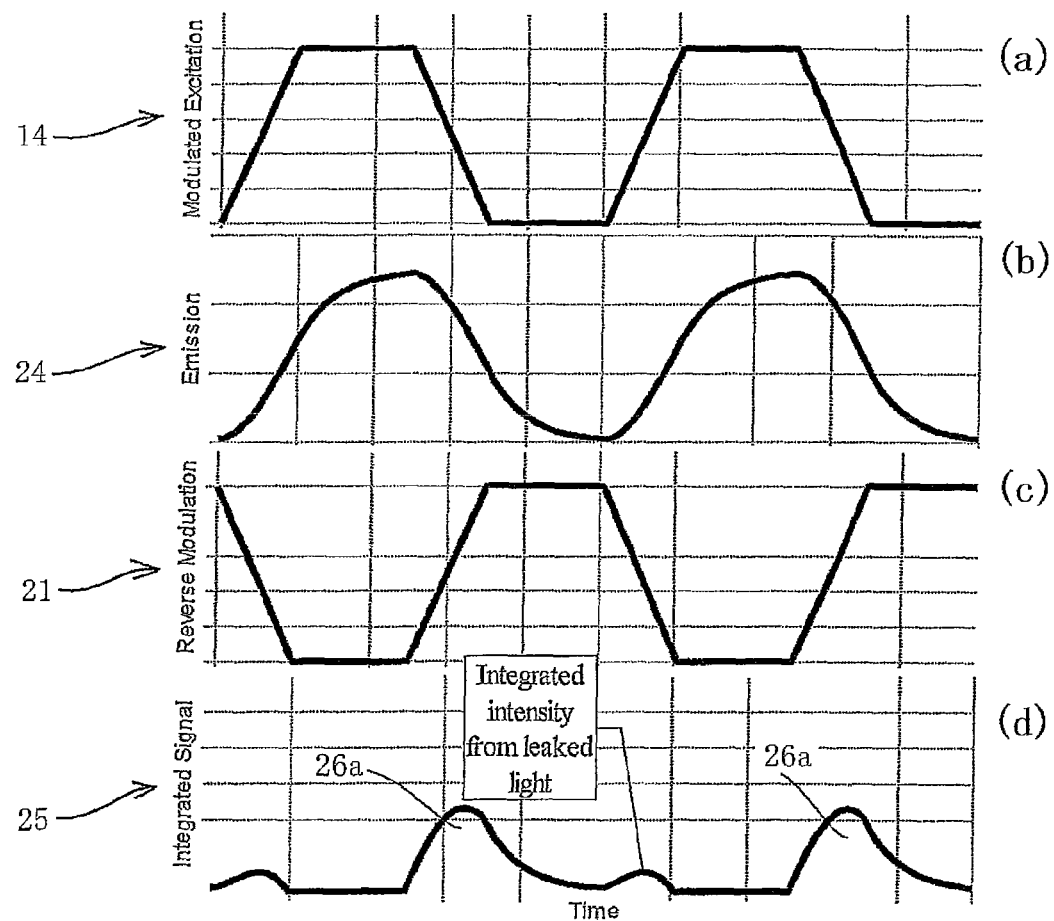
FIG. 13 Diagram showing the modulated excitation, the waveform emitted from the material, the detector side modulation and the resulting separation of the decaying emission, for the case of a trapezoidal waveform modulation.

As an example, the excitation light emitted by 11 is modulated by 12 resulting in a trapezoidal waveform shown in FIG. 13 (a). For this case, the light emitted by the material is shown in (b). A similar trapezoidal modulation is applied on the detector side by 21 and shown in (c). The modulation waveforms of (a) and (c) are modulating and synchronized at the same frequency and mutually reverse in phase. The waveform of the resulting light 25 which has been extracted from the luminescence 24 before reaching the detecting device 23, is shown in (d).

Because the modulation waveform (c) overlaps waveform (b) modulating the emitted light (a), a portion of the light 26a of light 25 shown in (d) does not contain only light from the decaying intensity, but also contains some portion of the light emitted during excitation.

The same material properties used earlier, for carrier lifetime and emission probability shown in FIG. 9, are then used for the case described in FIG. 13 to simulate the resulting integrated intensity.

Figure 14:
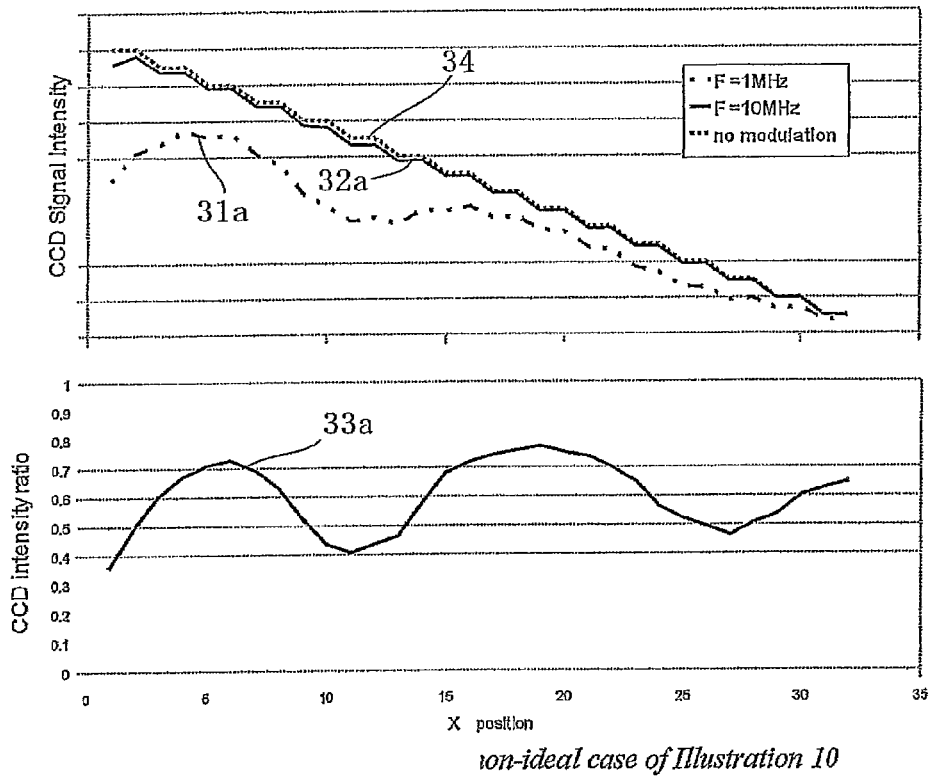
FIG. 14 Graph showing the integrated intensity as a function of position on the material simulated using the data of FIG. 9 for trapezoidal modulation for two frequencies and in the case of no modulation, and the ratio of the intensity taken at the two frequencies.

FIG. 14 shows the result of applying the waveforms of FIGS. 13 (a) and (c) at a frequency of 1 MHz, where the double dotted dashed line 31a represents the integrated intensity of the separated light 25 reaching the CCD detector. Again, for applying the modulation waveforms of Figures (a)

and (c) at a frequency of 10 MHz, the resulting integrated intensity curve 32a is plotted as a continuous line in the Figure.

The ratio of the intensity measured for 1 MHz modulation and the intensity measure for 10 MHz modulation is shown as trace 33a. This curve bears strong resemblance to the carrier lifetime data shown in FIG. 9. That is, even using the modulation characteristics of FIG. 13 and using the ratio of the intensity obtained at 2 different frequencies, the information pertaining to the carrier lifetime can be extracted.

Figure 15:
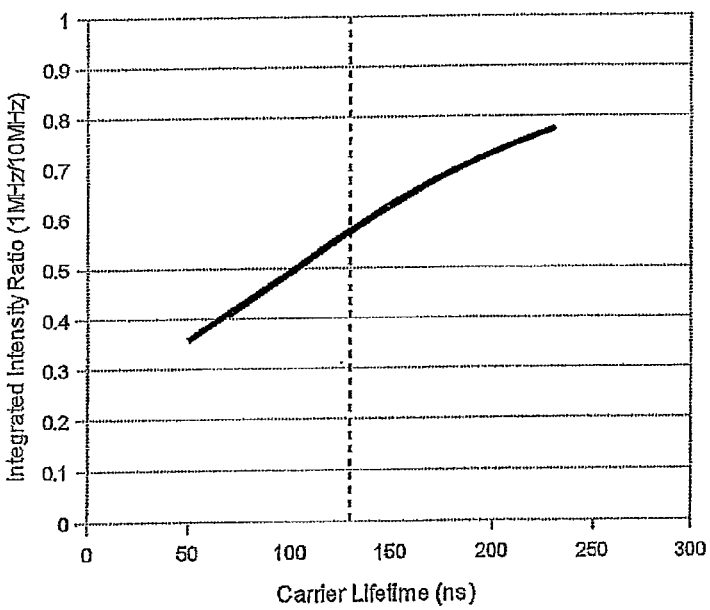
FIG. 15 Graph showing the relationship between the integrated intensity at a given frequency, which has been normalized with the intensity obtained at ten times that frequency, and carrier lifetime, in the case of trapezoidal modulation.

The ratio of the intensities measured for 1 MHz and 10 MHz modulation is plotted with respect to nominal carrier lifetime in FIG. 15. FIG. 15 was evaluated in the same way as FIG. 8. FIG. 15 shows that this ratio, based on the modulation properties described in FIG. 13, has a near linear relationship with the increase of the carrier lifetime, therefore showing the correspondence between the measured ratio and the carrier lifetime.

Again, ¼ of the light intensity emitted according to the continuous excitation described in FIG. 12 (b) is plotted in FIG. 14 as curve 34 as a function of position. The curve is essentially identical to the curve 32a for the above 10 MHz trapezoidal modulation. Therefore the ratio of the integrated intensity obtained using a trapezoidal modulation versus the integrated intensity measured for continuous excitation may also be used to extract the carrier lifetime information.

Figure 16:
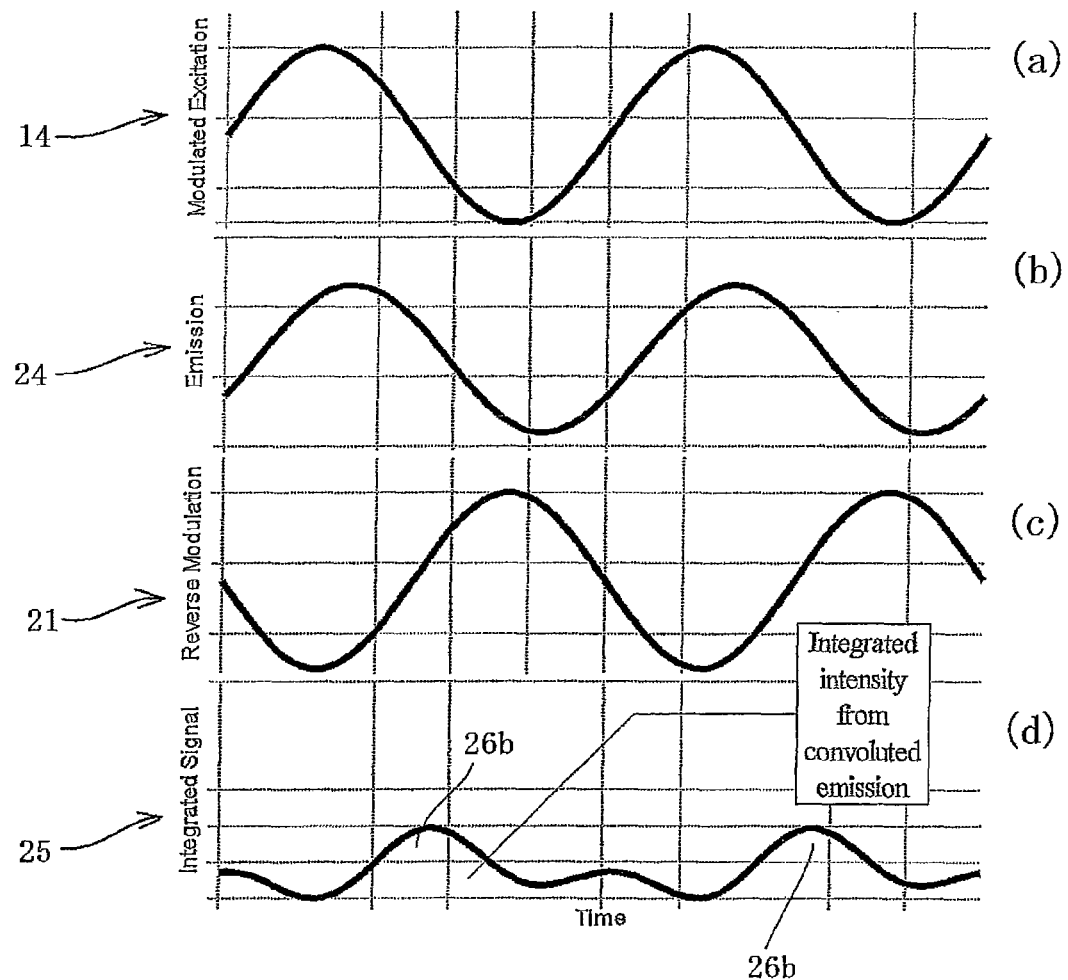
FIG. 16 Diagram showing the modulated excitation, the waveform emitted from the material, the detector side modulation and the resulting separation of the decaying emission, for the case of a sinusoidal waveform modulation.

In the simulation shown in FIG. 16, an excitation resembling a sinusoidal waveform is used and shown in (a). For this case, the light emitted by the material 24 is shown in (b). A similar sinusoidal modulation is applied on the detector side and shown in (c). The modulation waveforms of (a) and (c) are modulating and synchronized at the same frequency and mutually reverse in phase. The waveform of the resulting light 25 which has been extracted from the luminescence 24 before reaching the detecting device 23, is shown in (d).

Again because the modulation waveform (c) overlaps the waveform (b) modulating the emitted light (a), a portion of the light 26a of light 25 shown in (d) does not contain only light from the decaying intensity, but also contains some portion of the light emitted during excitation.

Figure 17:
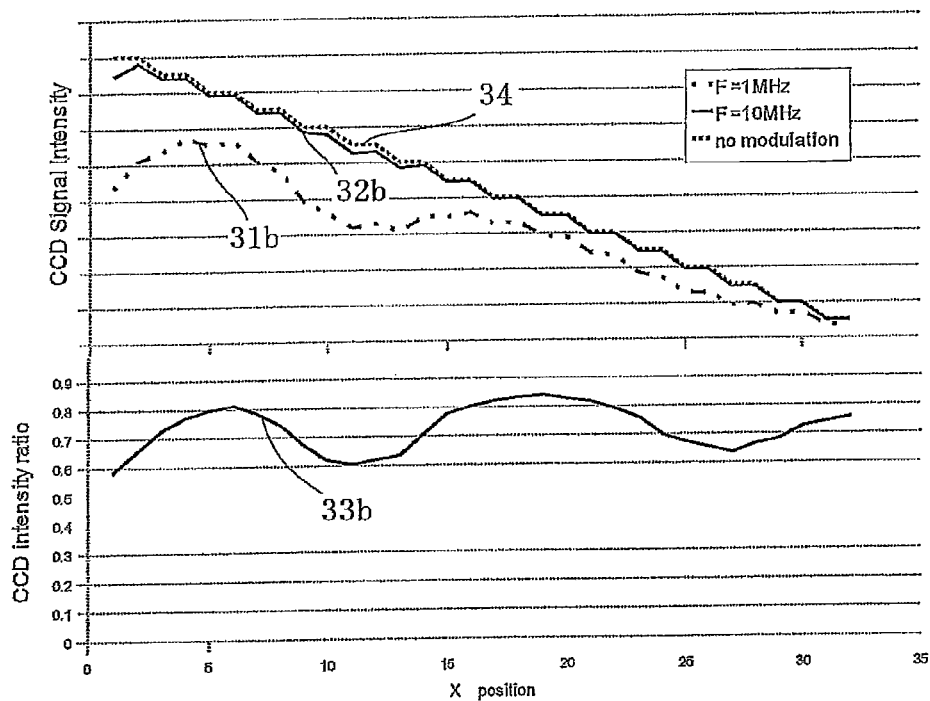
FIG. 17 Graph showing the integrated intensity as a function of position on the material simulated using the data of FIG. 9 for sinusoidal modulation for the two frequencies and in the case of no modulation, and the ratio of the intensity taken at the two frequencies.

In FIG. 17, the curve 31b representing integrated intensity obtained from the sinusoidal modulation of FIG. 16 at 1 MHz, the curve 32b of that obtained from at 10 MHz for a similar modulation, and curve 33b obtained from the ratio of curves 31b and 32b are shown. This resulting curve 33b closely resembles the carrier lifetime component of the material data of FIG. 9, showing that it is possible to extract the information related to the carrier lifetime.

Again, if the curve 31b is normalized using curve 34 representing ¼ of the intensity obtained in continuous excitation, the resulting characteristics also resemble those of curve 33b.

Figure 18:
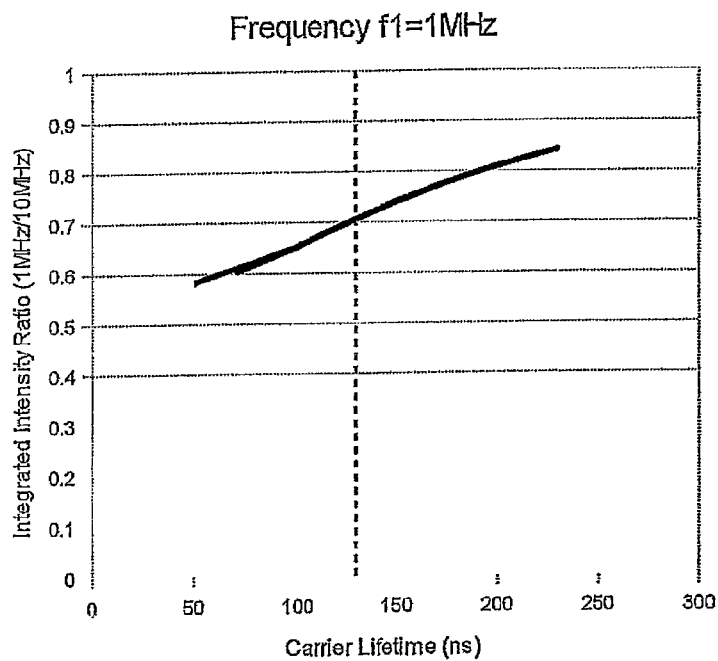
FIG. 18 Graph showing the relationship between the integrated intensity at a given frequency, which has been normalized with the intensity obtained at ten times that frequency, and carrier lifetime, in the case of sinusoidal modulation.

FIG. 18 shows a near linear relationship between the carrier lifetime and the ratio of two integrated intensities measured at frequencies 1 MHz and 10 MHz, as well as the ratio of these frequencies. FIG. 18 hence shows that even for a sinusoidal modulation the measurement and ratio of 2 different modulation frequencies has a correspondence to the information relating to the carrier lifetime.

In the following, other methods where normalizing the measured intensity using the ratio of 2 modulation, such as in the above using different frequencies or by using ¼ of the continuous excitation intensity, in order to remove the emission intensity dependence and extract the carrier lifetime are given.

Figure 19:
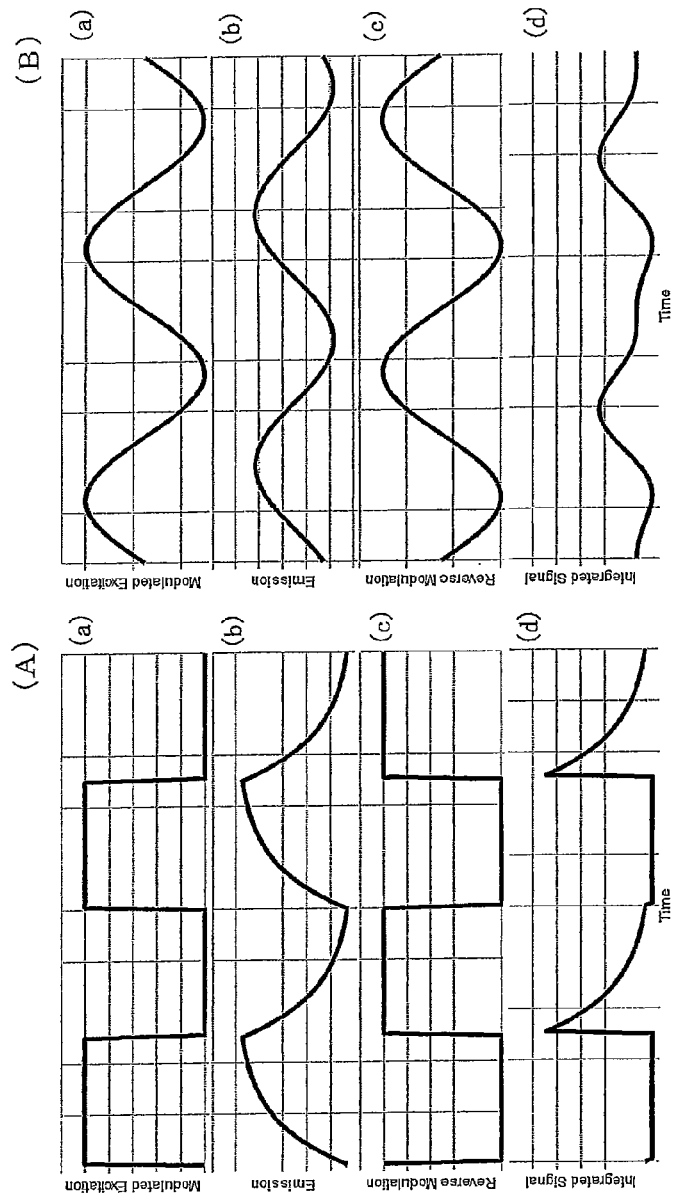
FIG. 19 Diagram showing the modulated excitation, the waveform emitted from the material, the detector side modulation and the resulting separation of the decaying emission, for a square waveform compared to a sinusoidal waveform at the same frequency.

The simulation described by FIG. 19 is the case where the ratio of the intensities is taken between two different waveforms.

The modulation waveforms of FIG. 19 (A) are the same as those of 10 (A). A square wave excitation modulation is shown in (a) and a square wave detection modulation in (c). The waveforms in (a) and (c) are synchronized at 1 MHz and mutually opposite in phase. The separated light to be accumulated by the CCD during the integration is shown in (d). The result of applying this to the material properties as a function of position is shown in curve 31c of FIG. 20 plotted as a double dotted dashed line.

The modulation waveforms of FIG. 19 (B) are the same as those of FIG. 16, where the excitation modulation (a) and the detection modulation (c) are sinusoidal curves. The modulations of (a) and (c) are applied at the same frequency and are phase shifted by 180 degrees. Further, they are applied at the same 1 MHz frequency as the square wave modulations of FIG. 19 (A) (a) and (c). The result of this sinusoidal modulation is shown as curve 32c in FIG. 20, plotted as a solid line.

Figure 20:
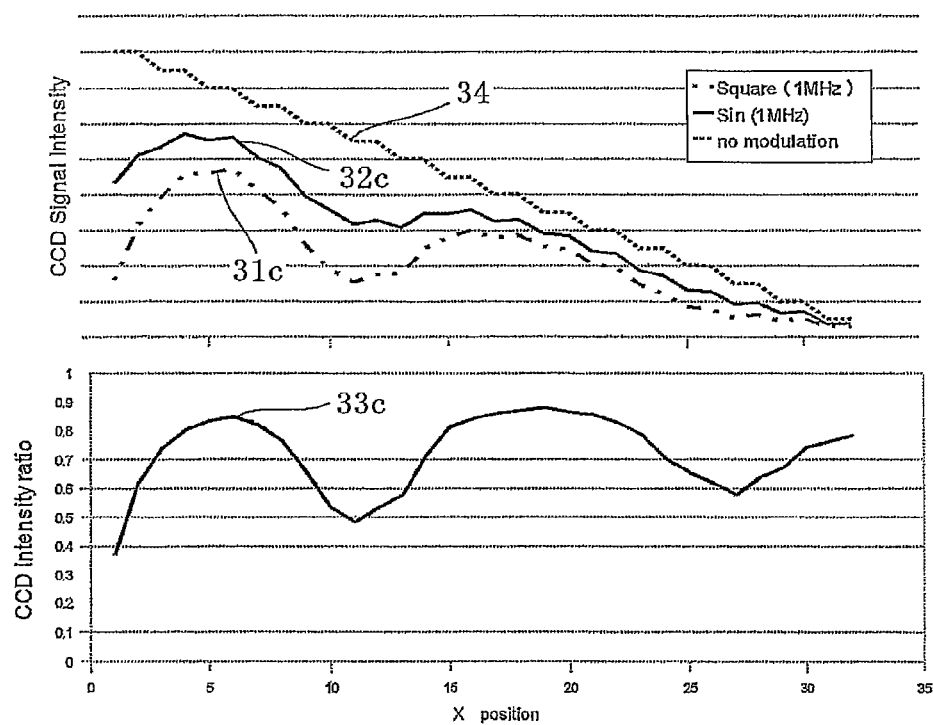
FIG. 20 Graph showing the integrated intensity as a function of position on the material simulated using the data of FIG. 9 for square modulation, sinusoidal modulation and in the case of no modulation for reference, and the ratio of the intensity taken at the two different waveforms.

The ratio of the square wave modulated intensity 31c versus the sinusoidal wave modulated intensity 32c is shown as curve 33c of FIG. 20. It shows that this curve closely resembles the curve describing the carrier lifetime material data of FIG. 9.

Figure 21:
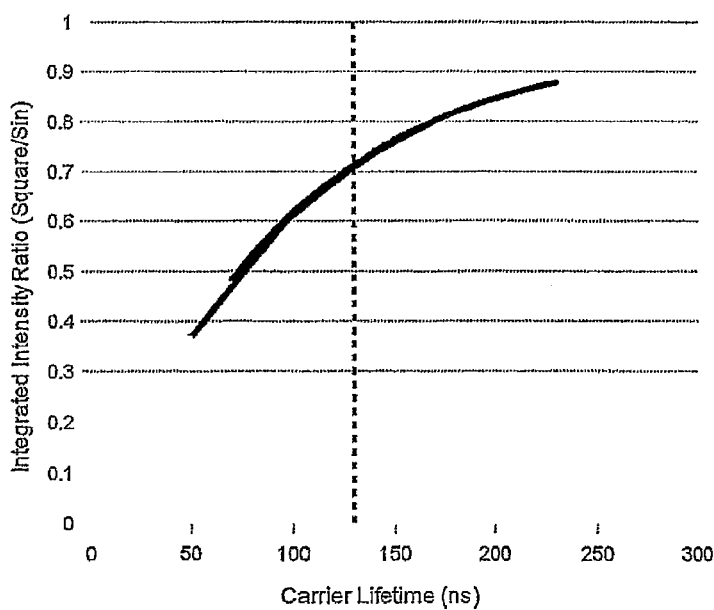
FIG. 21 Graph showing the relationship between the integrated intensity at a given frequency using a square modulation, which has been divided by the intensity obtained using a sinusoidal waveform, and carrier lifetime.

The ratio of the square wave modulated intensity versus the sinusoidal wave modulated intensity is plotted in FIG. 21 with respect to nominal carrier lifetime. From FIG. 21, we see that the trend for increased intensity ratio corresponds to the increasing carrier lifetime.

Figure 22:
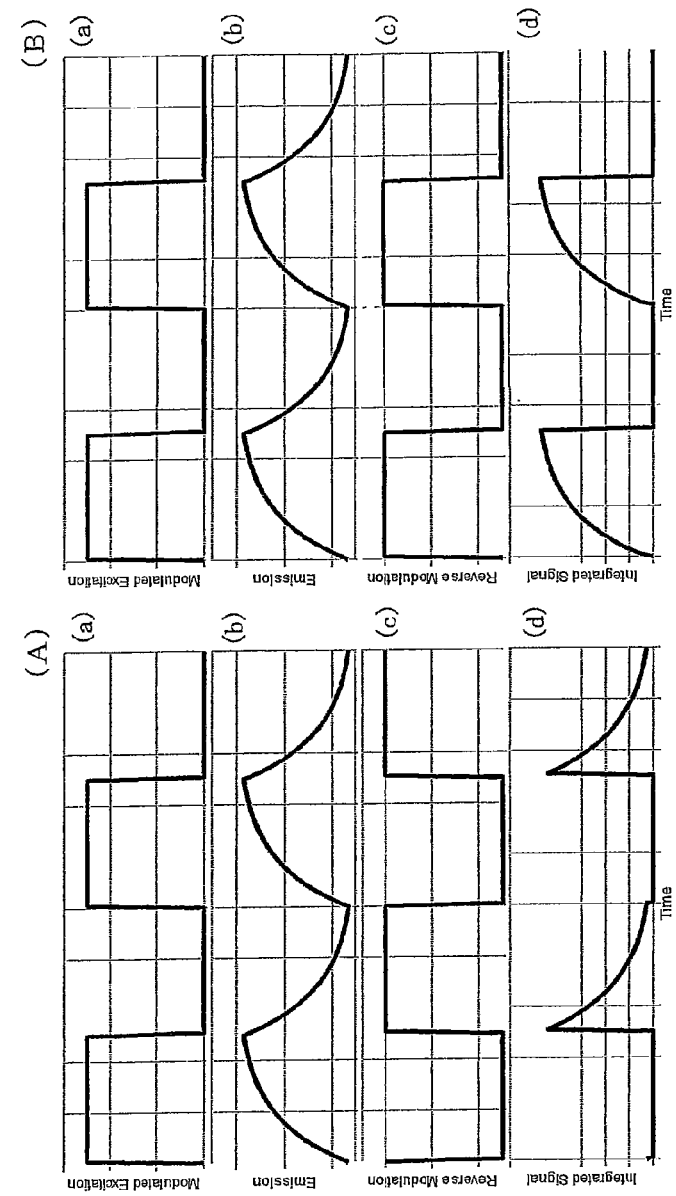
FIG. 22 Diagram showing the modulated excitation, the waveform emitted from the material, the detector side modulation and the resulting separation of the decaying emission, for two waveforms where the detector side modulation is relatively phase shifted.

The simulation described by FIG. 22 is the case where the ratio of the intensities is taken between two waveforms but for which the relative phase between the excitation modulation waveform and the detection modulation waveforms are offset.

The modulation waveforms of FIG. 22 (A) are the same as those of 10 (A) or 19 (A). The square waveforms in (a) and (c) are synchronized at 1 MHz and mutually phase shifted by 180 degrees. The separated light to be accumulated by the CCD during the integration is shown in (d). The result of applying this to the material properties as a function of position is shown in curve 31d of FIG. 23 plotted as a double dotted dashed line.

The modulation waveforms of FIG. 22 (B) display zero mutual phase shift. Both waveforms shown in (a) and (c) are square waves of duty ratio 50% applied synchronously at 1 MHz. The resulting distribution of applying this to the material properties is shown in FIG. 32d of FIG. 23.

Figure 23:
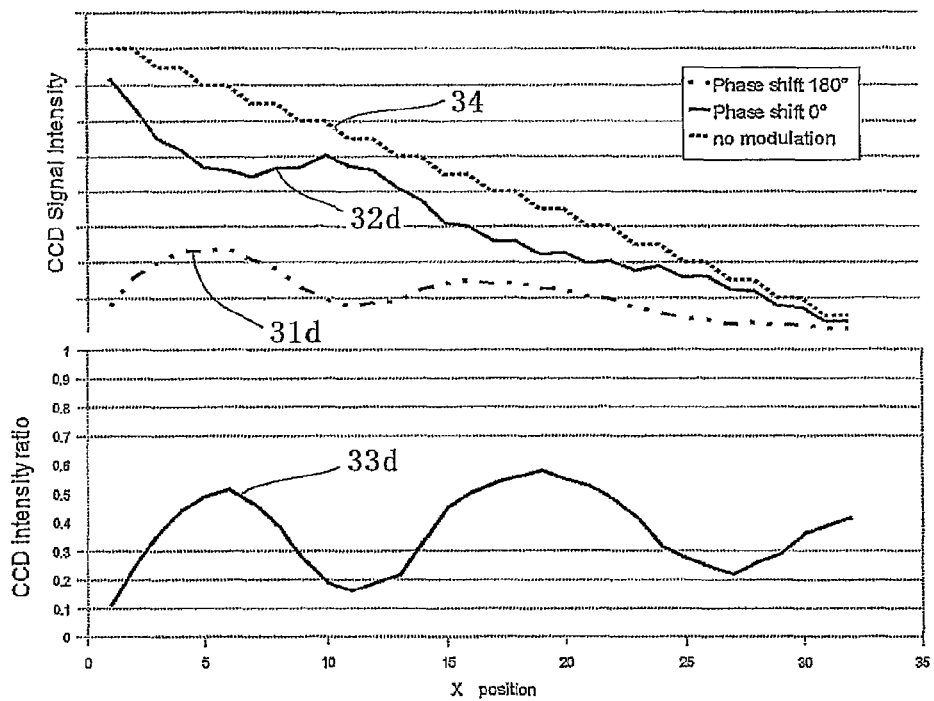
FIG. 23 Graph showing the integrated intensity as a function of position on the material simulated using the data of FIG. 9 for two different phase shifted modulations, the case of no modulation for reference, and the ratio of the intensity taken at the two different waveforms.

The ratio of the modulated intensity 31d versus the modulated intensity 32d is shown as curve 33d of FIG. 23. It shows that this curve closely resembles the curve describing the carrier lifetime material data of FIG. 9.

Figure 24:
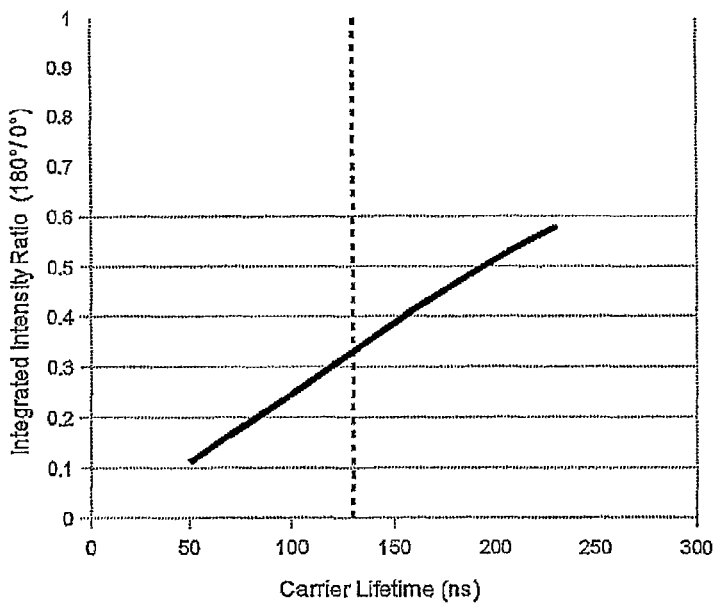
FIG. 24 Graph showing the relationship between the integrated intensity at a given frequency using a square modulation, which has been divided by the intensity obtained using a relatively phase-shifted waveform, and carrier lifetime.

FIG. 24 shows the relationship between nominal carrier lifetime and the ratio (integrated intensity resulting from modulations of FIG. 22 (A)/integrated intensity resulting from modulations of FIG. 22 (B)). From FIG. 24 we see that the carrier lifetime information can be extracted using the ratio of integrated intensities measured using different relatively phase-shifted square waves modulations on the detection side (c) with respect to the excitation square waves (a).

Figure 25:
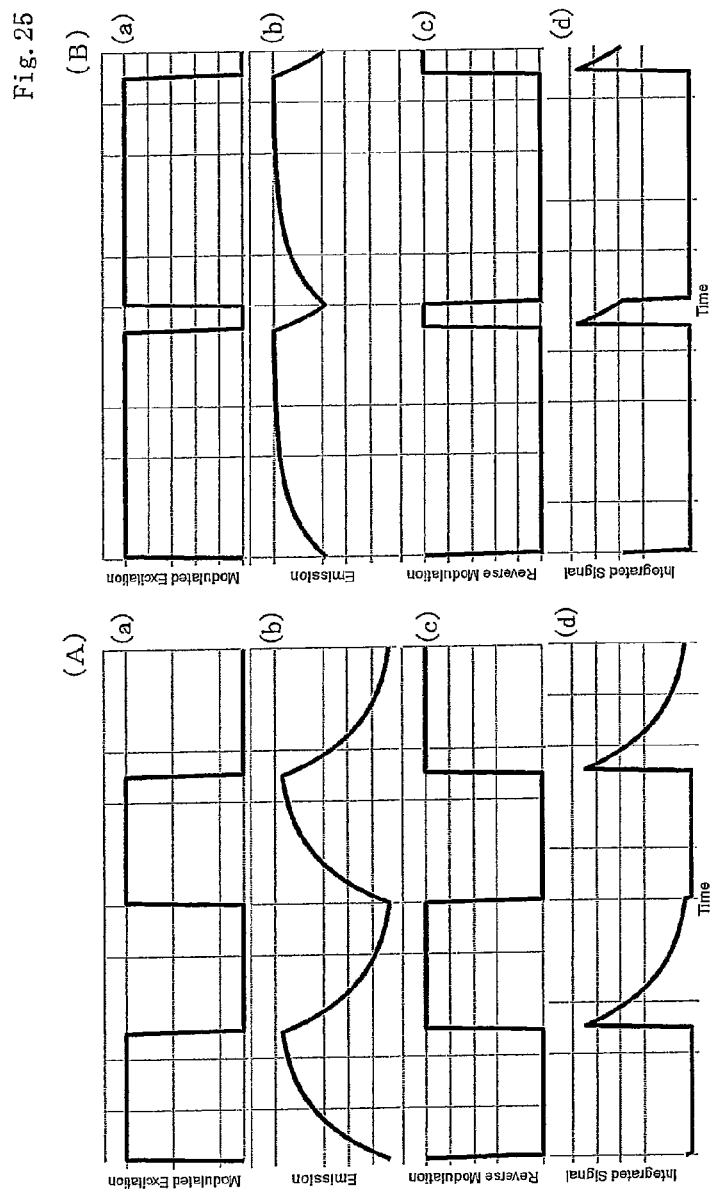
FIG. 25 Diagram showing the modulated excitation, the waveform emitted from the material, the detector side modulation and the resulting separation of the decaying emission, for two square waveforms where at two different duty-ratios, while keeping the reverse phase modulation between excitation and detection.
Figure 26:
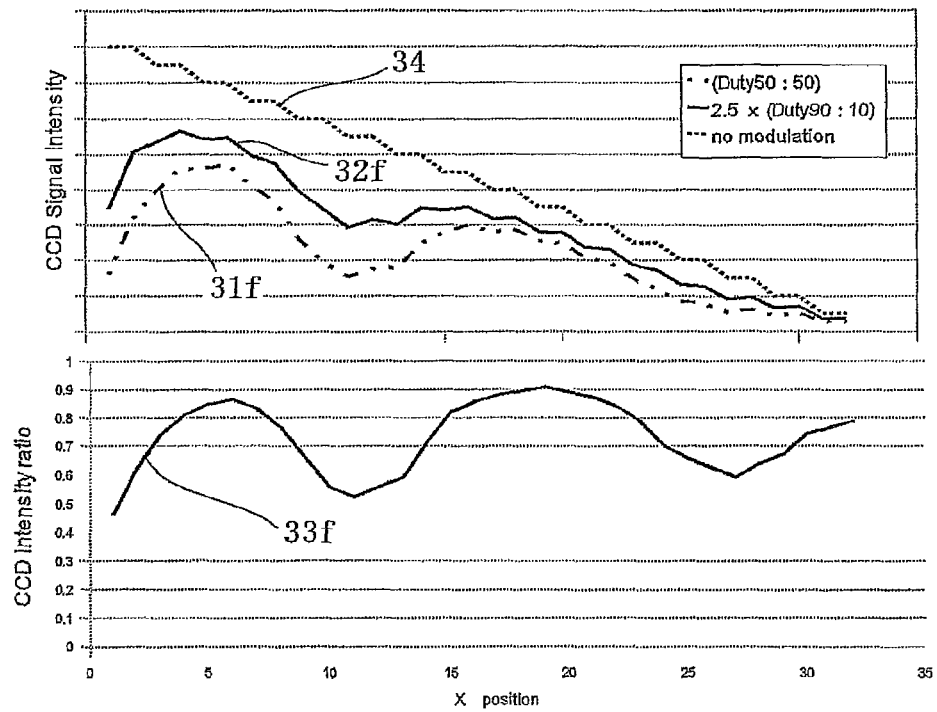
FIG. 26 Graph showing the integrated intensity as a function of position on the material simulated using the data of FIG. 9 for square waveforms at different duty-ratios, the case of no modulation for reference, and the ratio of the intensity taken at the two different waveforms.

The simulation described by FIGS. 25 to 26 demonstrate how the carrier lifetime information, from the material data of FIG. 9, can be extracted using the ratio of measured intensities from modulations having different duty ratios.

The modulation waveforms of FIG. 25 (A) are the same as those of FIG. 10 (A), 19 (A) or 21 (A), where the excitation modulation is shown in (a) and the detection modulation is shown in (c) are mutually inverted square waves synchronized at 1 MHz. The modulation waveforms of FIG. 25 (B) are also mutually inverted square waves synchronized at 1 MHz with excitation modulation shown in (a) and detection modulation shown in (c). However, compared to FIG. 25 (A) which shows modulations with duty ratio of 50:50, those in FIG. 25 (B) have a modulation duty ratio of 90:10.

In FIG. 26, the intensity integrated over the modulation described by 25 (A) is plotted as a double dotted dashed line 31$f$, and the intensity integrated over the modulation described by 25 (B) is plotted as the continuous line 32$f$. Again the ratio of curves 31$f$ and 32$f$ is shown as 33$f$. Again, the curve 33$f$ is seen to closely resemble the curve describing the carrier lifetime material data of FIG. 9.

Figure 27:
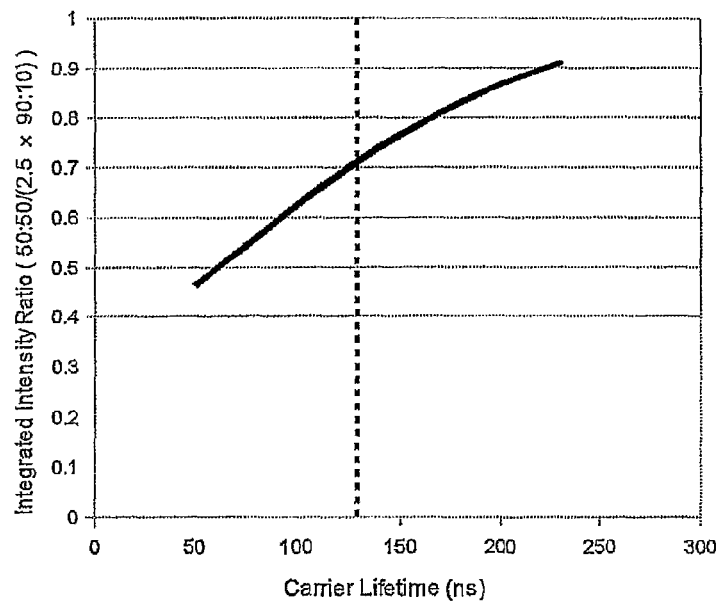
FIG. 27 Graph showing the relationship between the integrated intensity at a given frequency using a square modulation with duty 50:50, which has been divided by the intensity obtained using a square modulation with duty 90:10, and carrier lifetime.

FIG. 27 shows the relationship between nominal carrier lifetime and the ratio (integrated intensity resulting from modulations of FIG. 25 (A)/integrated intensity resulting from modulations of FIG. 25 (B)). From FIG. 27 we see that the carrier lifetime information can be extracted using the ratio of intensities measured using modulation waveforms of different duty ratios.

Each of the above embodiments were described in the following example configurations.
(1) The case where the ratio of measured intensity is taken for two different modulation frequencies
(2) The case where the ratio of intensities is obtained by dividing the intensity measured during modulation by the intensity obtained during continuous excitation.
(3) The case where the modulation are not described by square waveforms on either the excitation side or the detection side.
(4) The case where the ratio of intensities is obtained from two modulations with waveforms having different relative phase shifts.
(5) The case where the ratio of intensities is obtained from two modulations having different phase shifts between the excitation modulations with respect to the detection modulation.
(6) The case where the ratio of intensities is obtained from modulations having two different duty ratios.

Figure 28:
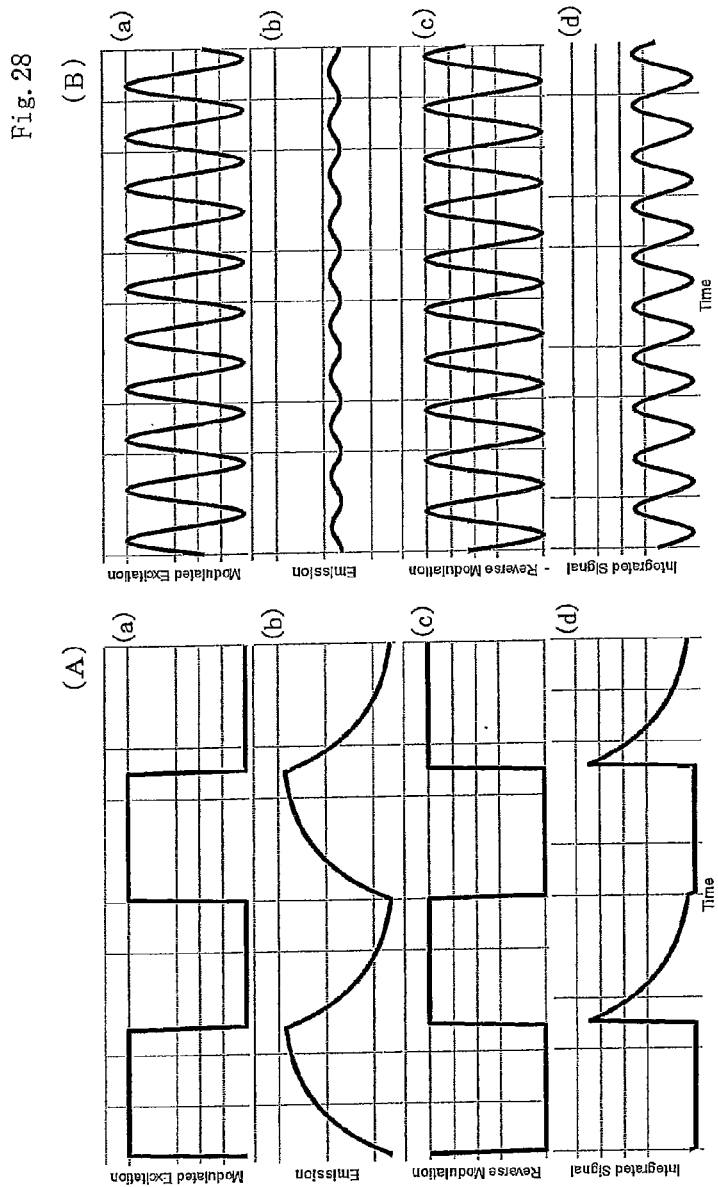
FIG. 28 Diagram showing the modulated excitation, the waveform emitted from the material, the detector side modulation and the resulting separation of the decaying emission, for two different waveforms and two different frequencies.

It is also possible to combine the above conditions. For example, the ratio of the intensity obtained using a square wave modulation at 1 MHz shown in FIG. 28 (A) with respect to the intensity obtained using a sinusoidal wavelength modulated at 10 MHz shown in FIG. 29 (B), can also be used to extract the information pertaining to the carrier lifetime.

Figure 29:
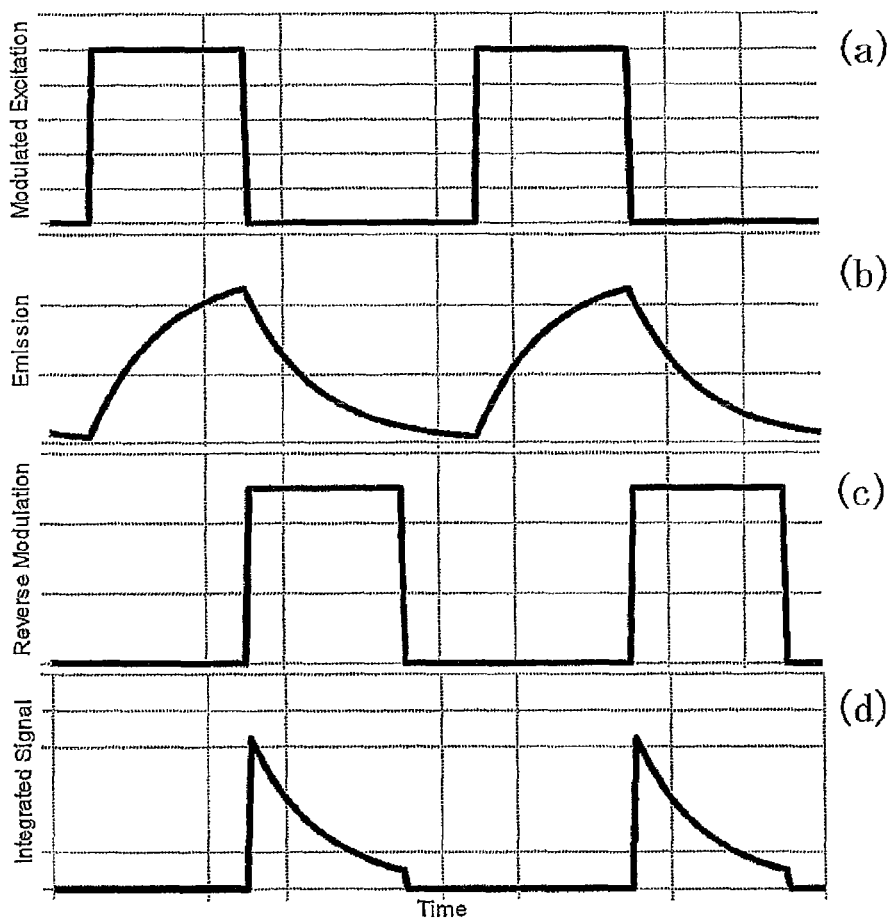
FIG. 29 Diagram showing the modulated excitation, the waveform emitted from the material, the detector side modulation and the resulting separation of the decaying emission, for the case of a square wave with duty ration other than 50:50.

Again, in the examples such as shown in FIGS. 5 and 10 (A), it was shown that the light emitted during material excitation and the decaying intensity occurring after the excitation could be separated using two square waves, at 50% duty and opposite phase, applied as the excitation modulation (a) and the detection modulation (c). Regarding this, as the example describe by FIG. 29, the duty ratio and phase shifts are not limited to 50% and 180 degrees. In the example of FIG. 29, with duty ratio of 40% and a phase shift of 144 degrees between the excitation and the detection modulation, it is also still possible to separate the component of the decaying emission.

Figure 30:
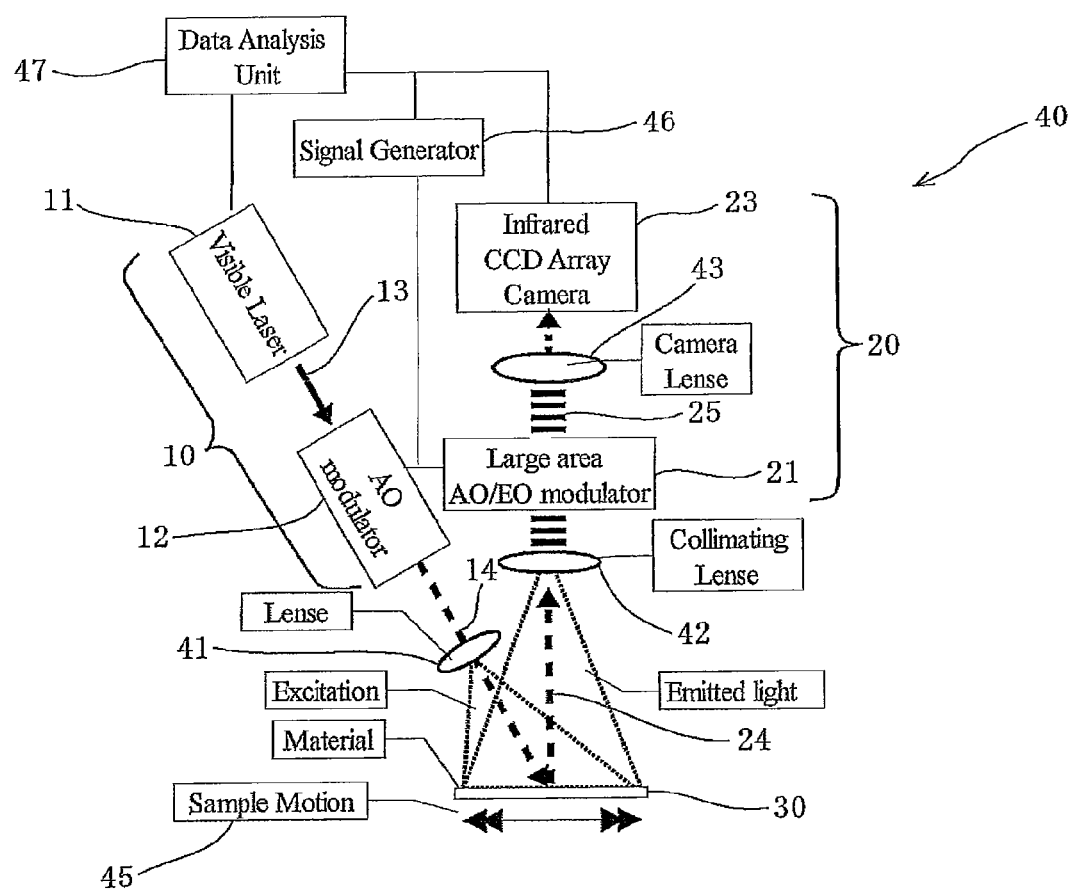
FIG. 30 A block diagram showing a first embodiment of the measurement method and measuring apparatus in an ideal configuration.

The apparatus 40 in the preferred embodiment of FIG. 30 describes the ideal configuration for implementing the measurement method described up to this point.

Just as for the apparatus 1 of the basic embodiment of FIG. 4, the excitation apparatus 10 is made up of an excitation source 11 and an excitation modulation device 12. The excitation source 11 is a solid state laser and the modulation device 12 an acousto-optic modulator. The light 13 emitted by the excitation source, modulated by 12 becomes the modulated excitation light 14.

The lens 41 placed after the modulation device 12 serves to guide the excitation light 14 onto a certain region in an area of the material 30. Lens 41 can be a collimator lens, a large focusing lens, a defocusing lens or a combination of these, such that the excitation is optimized at the position of material 30.

The detection apparatus 20 is made up of a modulation device 21 and a light detecting device 23. The modulation device 21 is an acousto-optic modulator. A collimator lens 42 is positioned between the material and the modulation device 21. The luminescence 24 emitted from the material 30 from a certain region passes through the collimator lens 42, some of that light passes through modulation device 21, such that the separated light 25 reaches the detecting device 23. The detecting device 23 is an array of detector cells from a CCD, before which a camera lens 43 is placed to focus the separated light 25. In addition, the detection device 21 can be equipped with filter 22 shown in FIG. 4 if necessary.

If the array of detector cells of the CCD detector device 23 are arranged in a two dimensional array, the luminescence 24 emitted from the material 30 from several positions in an area are integrated simultaneously by each of the CCD detector cell making it possible to obtain the carrier lifetime information and correlate that information with each position. Furthermore, for each of the CCD detector cell, the measured integrated intensity is processed and compared to obtain a distribution curve such as 33 in FIG. 11, in order to extract the information pertaining to the carrier lifetime of individual points within a large area on the material.

Again, if the array of detector cells of the CCD detector device 23 are arranged in a single or multiple rows, material 30 can be moved step-wise or continuously in a direction normal to these rows by a translation motion device 45, in such a way that the CCD detector device 23 may sequentially acquire luminescence from a large area of material 30. This can also be accomplished by fixing the position of material 30 while moving the measurement apparatus 40.

As shown in FIG. 30, the measurement apparatus 40 is equipped with a modulation control unit 46. From this control unit 46, the excitation modulation device 12 and the detector modulation device 21 are controlled, and as shown in each Figure, applies modulations to the excitation light and the emitted light.

The measurement apparatus 40 is also equipped with central control and processing unit 47, which controls the excitation source 11 as well as the modulation devices 12 and 21. Also, for each integration time during which the accumulated emission intensity is digitized by the CCD measurement device, saved to memory by the control and processing unit 47, where intensity ratios are taken resulting in curves such as shown in 33 of FIG. 11. For each detector cell of the CCD results a pixel with an intensity correlated to the carrier lifetime at a certain position within an area of material 30.

The information processed by unit 47 giving the carrier life time for positions on the material within a certain area can then be displayed as carrier lifetime values in a table, or the result can be represented as a shade in an image. In the latter case each of the CCD detector cells are represented by a pixel in that image.

Figure 31:
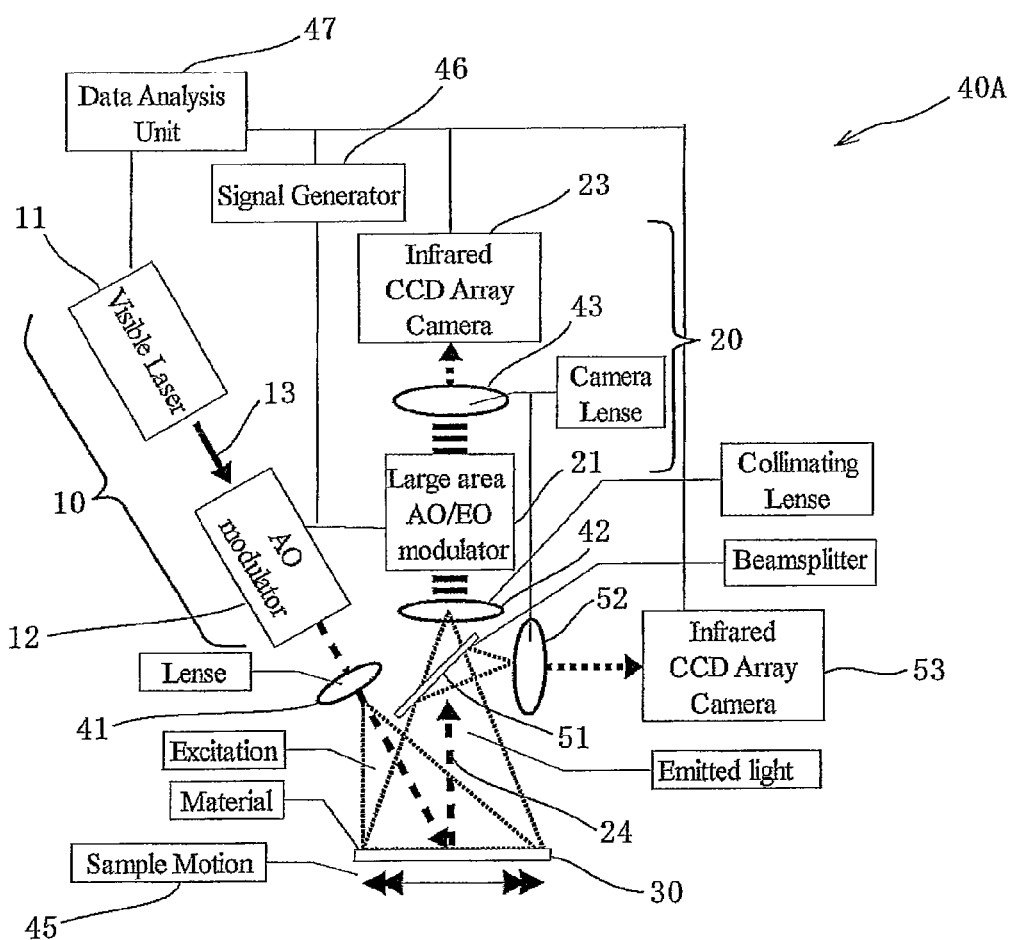
FIG. 31 A block diagram showing a second embodiment of the measurement method and measuring apparatus in an ideal configuration.

In FIG. 31, the measurement apparatus 40A is equipped with a beam splitter 51 to separate the luminescence 24 emitted from material 30, then the separated light is collimated using a second camera lens 52. This portion of the emitted light does not go through the detector modulation device, and is accumulated by a second measurement device 53. In measurement apparatus 40A, the accumulation of both a modulated intensity of the luminescence 24 and non-modulated intensity of the luminescence 24 can be performed in a single measurement.

A second modulation device could also be inserted between the beam splitter 51 and the detector device 53 in order to enable the measurement of two different modulations of the luminescence 24 in a single measurement.

In addition, a variety of modifications are possible, and the present invention is not limited to the above embodiments. For example if the excitation source 11 were an intermittently pulsed laser, then the modulation device 12 would not be required in order to obtain modulations with a variety of duty ratios. Again, if the detector device were such that it was possible to intermittently impede the signal from be accumulated into memory within that device, then even without the modulation device 21 it would be possible to isolate the decay luminescence, integrate that signal over a fixed integration time to similarly extract the carrier lifetime information.

It is also possible to replace the excitation source 10 with a device which is not a light source, but that can excite carriers within material 30 periodically using electrical excitation so that light is emitted during the electron-hole pair recombination via an electroluminescent process, thereby enabling measurement of the carrier lifetime.

The although the present invention's apparatus and measurement methods have foreseeable applications on typical materials such as silicon (Si), indium phosphide (InP), silicon carbide (SiC), gallium arsenide (GaAs), silicon germanium (SiGe), germanium (Ge), compound chalcopyrite (CuInS2), crystalline or polycrystalline chalcopyrite alloys (Cu(In,Ga)Se2), fullerenes (C60) and other organic semiconductors, it is not limited to such materials.

Also as long as some method of exciting carriers inside a material such that they eventually drop down to a lower energy level, were it optical or electrical, the applications can extend to materials such organic compounds and polymers.

REFERENCE SIGN'S LIST

1 Measurement apparatus
10 Excitation apparatus
11 Excitation source
12 Modulation device
13 Continuous light
14 Excitation light
20 Detector apparatus
21 Modulation device
22 Filter
23 Light accumulation device
24 Luminescence
25 Separated light
26 Decaying light
30 Semiconductor material
40 Measurement apparatus
41 Lens
42 Collimating lens
43 Camera lens
45 Translation device
46 Modulation control unit
47 Main control and processing unit
51 Beam splitter
52 Camera Lens
53 Light accumulation device

The invention claimed is:

1. A carrier lifetime measurement method comprising:
exciting a material such that excitation periods are repeated at periodic intervals;
optically separating decaying light emitted after the end of the excitation period from light emitted from the material during the excitation period;
accumulating a plurality of the separated decaying light emissions within a measurement time which spans a plurality of the excitation periods;
detecting the accumulated light; and
obtaining a lifetime based on an intensity of the accumulated light.

2. A carrier lifetime measurement method according to claim 1, wherein the decaying light is separated from the light emitted during the excitation period by starting to receive the light emitted from the material at the same time or after the end of the excitation period.

3. A carrier lifetime measurement method according to claim 1, wherein both a portion of the light emitted during the excitation period as well as the decaying light are separated from the remaining portion of the light emitted during the excitation period by starting to receive the light emitted from the material partway through the excitation period.

4. A carrier lifetime measurement method according to claim 1, wherein the excitation applied by an excitation source passes through an excitation modulation device to excite the material such that excitation periods are repeated at periodic intervals.

5. A carrier lifetime measurement method according to claim 1, wherein excitations are intermittently applied by an excitation source to excite the material such that excitation periods are repeated at periodic intervals.

6. A carrier lifetime measurement method according to claim 1, wherein the light emitted from the material is passed through a detection modulation device to separate the decaying light from the light emitted during the excitation period, and a plurality of the decaying light emission periods are accumulated and detected by a light detecting device during an integration time corresponding to the measurement time.

7. A carrier lifetime measurement method according to claim 6, wherein the light detecting device comprises a plurality of detector cells in an array, wherein a plurality of the decaying light emission periods are accumulated and detected by each detector cell.

8. A carrier lifetime measurement method according to claim 7, wherein the light detecting device comprises a plurality of detector cells arranged in a two dimensional array, wherein decaying light emitted from a certain region of the material is simultaneously received by each detector cell to obtain correlated information related to a position in the region and the carrier lifetime.

9. A carrier lifetime measurement method according to claim 7, wherein the light detecting device comprises a plurality of detector cells arranged in a line, and where the decaying light emitted from the material is simultaneously received by the plurality of detector cells and for which correlated information related to positions in the certain region of the material and the carrier lifetime is obtained by moving the line of detectors.

10. A carrier lifetime measurement method according to claim 1, wherein a light detecting device capable of intermittently receiving the light emitted from the material is used to separate the decaying light from the light emitted during the excitation period and to accumulate and detect a plurality of the decaying light emission periods during the measurement time.

11. A carrier lifetime measurement method according to claim 1, wherein the material is excited at a plurality of frequencies to obtain accumulated decaying light emission intensities from the material, where these intensities are normalized to remove the emission intensity component by computing a ratio of intensities measured at different frequencies, in order to isolate and quantify the carrier lifetime component of the intensities.

12. A carrier lifetime measurement method according to claim 1, wherein a carrier lifetime component is isolated, the emission intensity component is removed by taking a ratio of an intensity of the detected light obtained by accumulating the decaying periods with the intensity obtained when the material is being excited, and wherein the normalization intensity is obtained by continuously detecting the light emitted from the material while excitation are repeated at periodic intervals.

13. A carrier lifetime measurement method according to claim 1, wherein the applied material excitation is modulated at different waveforms to obtain the accumulated decaying light intensity emitted from the material excited by individual modulation waveforms, and where the emission intensity component is removed by computing the ratio of the detected light intensities resulting from modulations with different waveforms in order to isolate the carrier lifetime component.

14. A carrier lifetime measurement method according to claim 1, wherein the light emitted from the material is modulated by waveforms with different phases to obtain the accumulated decaying light intensity, and wherein the emission intensity component is removed by computing the ratio of the detected light intensities resulting from modulations with different phases in order to isolate the carrier lifetime component.

15. A carrier lifetime measurement method according to claim 1, wherein the duty ratio of the material excitation modulation, and the duty ratio of the light detection modulation during which the decaying light is separated from the light emitted during the excitation are both made different, and wherein the emission intensity component is removed by computing the ratio of the detected light intensities resulting from measurements where the duty ratios are different from each other in order to isolate the carrier lifetime component.

16. A carrier lifetime measurement method according to claim 1, wherein the excitation applied to the material is optical excitation.

17. A carrier lifetime measurement method according to claim 1, wherein the excitation applied to the material is electrical power excitation.

18. A carrier lifetime measurement apparatus for exciting a material and detecting light emitted from that material, comprising:
   an excitation apparatus for exciting the material such that excitation periods are repeated at periodic intervals; and
   a detection apparatus for separating the decaying light emitted after the end of the excitation period from the light emitted from the material during the excitation period and accumulating and detecting a plurality of the separated decaying light emissions within a measurement time which spans a plurality of the excitation periods.

19. A carrier lifetime measurement apparatus according to claim 18, wherein the excitation apparatus comprises an excitation source and an excitation modulation device for modulating an excitation emitted from the excitation source such that excitation periods are repeated at periodic intervals.

20. A carrier lifetime measurement apparatus according to claim 18, wherein the excitation apparatus comprises an excitation source for emitting excitations such that excitation periods are repeated at periodic intervals.

21. A carrier lifetime measurement apparatus according to claim 20, wherein the excitation source is optical in nature.

22. A carrier lifetime measurement apparatus according to claim 20, wherein the excitation source is electrical in nature.

23. A carrier lifetime measurement apparatus according to claim 18, wherein the detection apparatus comprises a modulation device for separating the light emitted from the material between light emitted during the excitation period and light emitted during the decaying period, and a light detecting device for accumulating and detecting light over a plurality of the decaying light emission periods during an integration time corresponding to the measurement time.

24. A carrier lifetime measurement apparatus according to claim 23, wherein the detection apparatus starts to receive the light emitted from the material at the same time or after the end of the excitation period to separate the decaying light from the light emitted during the excitation period.

25. A carrier lifetime measurement apparatus according to claim 23, wherein the light detecting device comprises a plurality of detector cells in an array, wherein a plurality of the decaying light emission periods are accumulated and detected by each detector cell.

26. A carrier lifetime measurement apparatus according to claim 25, wherein the light detecting device comprises a plurality of detector cells arranged in a two dimensional array, wherein the decaying light emitted from a certain region of the material is received by each of the detector cells to obtain correlated information related to a position in the region and the carrier lifetime.

27. A carrier lifetime measurement apparatus according to claim 25, wherein the light detecting device comprises a plurality of detector cells arranged in a line and a translation motion device is provided for changing the position of the light detecting device relative to the material in a direction normal to the line, wherein the decaying light emitted from the material is simultaneously received by the plurality of detector cells and for which correlated information related to a position in the certain region and the carrier lifetime is obtained by moving the line of detectors.

28. A carrier lifetime measurement apparatus according to claim 18, wherein the detection apparatus comprises a light detecting device for intermittently receiving the light emitted from the material to separate the decaying light from the light emitted during the excitation period, detecting and accumulating over a plurality of decaying light emission periods.

29. A carrier lifetime measurement apparatus according to claim 28, wherein the detection apparatus starts to receive the light emitted from the material partway through the excitation period to separate a portion of the light emitted during the excitation period and the decaying light from a remaining portion of the light emitted during the excitation period.

30. A carrier lifetime measurement apparatus according to claim 18, wherein a wavelength filter is positioned between the material and the detection apparatus.

31. A carrier lifetime measurement apparatus according to claim 18, wherein a polarization filter is positioned between the material and the detection apparatus.

32. A carrier lifetime measurement apparatus according to claim 18, wherein the excitation apparatus is capable of changing the frequency of the excitation applied to the material, and
   wherein the excitation apparatus comprises a central control and processing unit for normalizing the signal obtained by the detection apparatus to remove the emission intensity component, in order to isolate the carrier lifetime component by computing the ratio of detected light intensities resulting from excitations at different frequencies.

33. A carrier lifetime measurement apparatus according to claim 18, wherein the excitation apparatus is capable of exciting the material such that excitation periods are repeated at periodic intervals, and wherein the excitation apparatus comprises a central control and processing unit for normalizing the signal obtained by the detection apparatus to remove the emission intensity component, in order to isolate the carrier lifetime component by computing the ratio of detected light intensities resulting from measurements as described above to light intensities resulting from continuous detection of the light emitted from the material.

34. A carrier lifetime measurement apparatus according to claim 18, wherein the detection apparatus is capable of modulating, detecting and accumulating the decaying light emissions for which the excitations applied to the material have been modulated by different waveforms, and wherein the detection apparatus comprises a central control and processing unit for normalizing the signal obtained by the detection apparatus to remove the emission intensity component, by computing the ratio of detected light intensities resulting from modulations with different waveforms.

35. A carrier lifetime measurement apparatus according to claim 18, wherein the detection apparatus is capable of modulating, detecting and accumulating the decaying light emissions for which the excitations applied to the material have been modulated by waveforms at different phases, and wherein the detection apparatus comprises a central control and processing unit for normalizing the signal obtained by the detection apparatus to remove the emission intensity component, by computing the ratio of detected light intensities resulting from modulations with waveforms at different phases.

36. A carrier lifetime measurement apparatus according to claim 18, wherein the excitation apparatus is capable of changing a duty ratio of the periodic excitations applied of the material, and the detection apparatus is capable of changing its duty ratio of the period during which the decaying light is separated from the light emitted during the excitation period, and wherein the excitation apparatus comprises a central control and processing unit for normalizing the signal obtained by the detection apparatus to remove the emission intensity component, by computing the ratio of detected light intensities resulting from modulations with waveforms of different duty ratios.

* * * * *